(12) United States Patent
Yadidi

(10) Patent No.: US 10,149,823 B2
(45) Date of Patent: Dec. 11, 2018

(54) DRY POWDER FORMULATIONS AND METHODS OF USE

(71) Applicant: OtiTopic, Inc., Los Angeles, CA (US)

(72) Inventor: Kambiz Yadidi, Los Angeles, CA (US)

(73) Assignee: OTITOPIC INC., Los Angeles, CA (US)

( * ) Notice: Subject to any disclaimer, the term of this patent is extended or adjusted under 35 U.S.C. 154(b) by 0 days.

(21) Appl. No.: 13/949,862

(22) Filed: Jul. 24, 2013

(65) Prior Publication Data
US 2014/0322328 A1    Oct. 30, 2014

Related U.S. Application Data

(60) Provisional application No. 61/817,435, filed on Apr. 30, 2013.

(51) Int. Cl.
| | | |
|---|---|---|
| *A61K 9/14* | (2006.01) | |
| *A61P 7/02* | (2006.01) | |
| *A61K 9/00* | (2006.01) | |
| *A61M 15/00* | (2006.01) | |
| *A61K 31/616* | (2006.01) | |

(52) U.S. Cl.
CPC .......... *A61K 9/0075* (2013.01); *A61K 31/616* (2013.01); *A61M 15/0045* (2013.01); *A61K 9/14* (2013.01); *A61M 2202/064* (2013.01); *A61P 7/02* (2018.01); *Y10S 514/958* (2013.01); *Y10T 428/2982* (2015.01)

(58) Field of Classification Search
USPC .......................................... 424/489; 514/958
See application file for complete search history.

(56) References Cited

U.S. PATENT DOCUMENTS

| | | | |
|---|---|---|---|
| 3,906,950 A | 9/1975 | Cocozza | |
| 4,353,365 A | 10/1982 | Hallworth et al. | |
| 4,885,287 A | 12/1989 | Hussain et al. | |
| 4,995,385 A | 2/1991 | Valentini et al. | |
| 5,256,538 A * | 10/1993 | Aiken | C07K 16/28 435/7.1 |
| 5,327,883 A | 7/1994 | Williams et al. | |
| 5,506,203 A | 4/1996 | Backstrom et al. | |
| 5,518,998 A | 5/1996 | Backstrom et al. | |
| 5,639,441 A | 6/1997 | Sievers et al. | |
| 5,673,686 A | 10/1997 | Villax et al. | |
| 5,750,559 A | 5/1998 | Bianco | |
| 5,855,913 A | 1/1999 | Hanes et al. | |
| 5,874,064 A | 2/1999 | Edwards et al. | |
| 5,875,776 A | 3/1999 | Vaghefi | |
| 6,051,256 A | 4/2000 | Platz et al. | |
| 6,051,566 A * | 4/2000 | Bianco | A61K 31/192 514/165 |
| 6,136,295 A | 10/2000 | Edwards et al. | |
| 6,136,346 A | 10/2000 | Eljamal et al. | |
| 6,187,344 B1 | 2/2001 | Eljamal et al. | |
| 6,254,854 B1 | 7/2001 | Edwards et al. | |
| 6,284,282 B1 | 9/2001 | Maa et al. | |
| 6,309,623 B1 | 10/2001 | Weers et al. | |
| 6,358,530 B1 | 3/2002 | Eljamal et al. | |
| 6,408,846 B1 | 6/2002 | Ohki et al. | |
| 6,423,344 B1 | 7/2002 | Platz et al. | |
| 6,455,028 B1 | 9/2002 | Wulfhart et al. | |
| 6,503,480 B1 | 1/2003 | Edwards et al. | |
| 6,561,186 B2 | 5/2003 | Casper et al. | |
| 6,565,885 B1 | 5/2003 | Tarara et al. | |
| 6,569,406 B2 | 5/2003 | Stevenson et al. | |
| 6,592,904 B2 | 7/2003 | Platz et al. | |
| 6,630,169 B1 | 10/2003 | Bot et al. | |
| 6,638,495 B2 | 10/2003 | Weers et al. | |
| 6,652,837 B1 | 11/2003 | Edwards et al. | |
| 6,705,313 B2 | 3/2004 | Niccolai | |
| 6,732,732 B2 | 5/2004 | Edwards et al. | |
| 6,737,042 B2 | 5/2004 | Rabinowitz et al. | |
| 6,766,799 B2 | 7/2004 | Edwards et al. | |
| 6,848,197 B2 * | 2/2005 | Chen et al. | 34/373 |
| 6,880,555 B1 | 4/2005 | Brunnberg et al. | |
| 6,881,398 B2 | 4/2005 | Myrman et al. | |
| 6,884,794 B2 | 4/2005 | Staniforth et al. | |
| 6,893,657 B2 | 5/2005 | Roser et al. | |
| 6,979,437 B2 * | 12/2005 | Bartus et al. | 424/45 |
| 6,994,842 B2 | 2/2006 | Lee et al. | |
| 6,998,137 B2 | 2/2006 | Shih et al. | |
| 7,025,059 B2 | 4/2006 | Pera | |
| 7,089,934 B2 | 8/2006 | Staniforth et al. | |
| 7,146,978 B2 | 12/2006 | Edwards et al. | |
| 7,189,750 B2 | 3/2007 | Assaf et al. | |
| 7,201,929 B2 | 4/2007 | Finkelstein | |
| 7,205,343 B2 | 4/2007 | Dellamary et al. | |
| 7,267,813 B2 | 9/2007 | Watanabe et al. | |
| 7,278,425 B2 | 10/2007 | Edwards et al. | |
| 7,284,553 B2 | 10/2007 | Hochrainer | |
| 7,306,787 B2 | 12/2007 | Tarara et al. | |
| 7,405,207 B2 | 7/2008 | Leonard et al. | |

(Continued)

FOREIGN PATENT DOCUMENTS

| | | |
|---|---|---|
| CN | 1503661 A | 6/2004 |
| CN | 101909650 A | 12/2010 |

(Continued)

OTHER PUBLICATIONS

Hadinoto et al. (2007). Dry powder aerosol delivery of large hollow nanoparticulate aggregates as prospective carriers of nanoparticulate drugs: Effects of phospholipids. International Journal of Pharmaceutics, 33: 187-198.*

Roth, G. J. and Calverley, D. C. (1994). Aspirin, Platelets, and Thrombosis: Theory and Practice. Blood, 83(4): 885-898.*

Miser (2011). "Appropriate Aspirin Use for Primary Prevention of Cardiovascular Disease." American Family Physician, 83(12): 1384-1386.*

(Continued)

*Primary Examiner* — Isaac Shomer
(74) *Attorney, Agent, or Firm* — FisherBroyles, LLP; James W. Hill

(57) ABSTRACT

A respirable dry powder can include acetylsalicylic acid or a pharmaceutically acceptable salt thereof. The dry powder can include a mixture of: (i) dry particles have a volume median geometric diameter (VMGD) less than 5 μm; and (ii) dry particles have a volume median geometric diameter (VMGD) of about 15 μm or more.

12 Claims, 2 Drawing Sheets

(56) References Cited

U.S. PATENT DOCUMENTS

Figure 1:
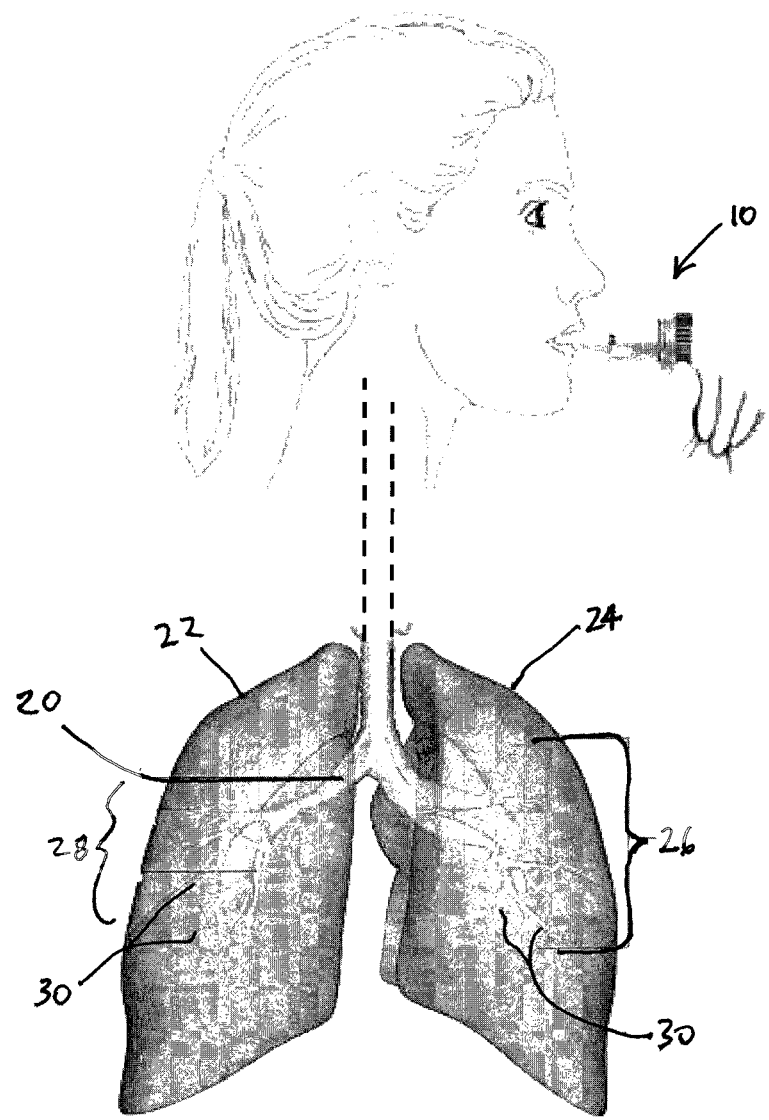
Figure 2A:
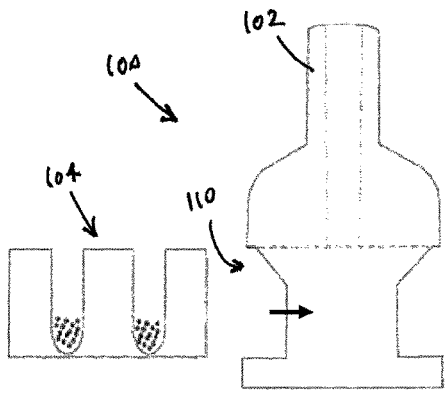
Figure 2B:
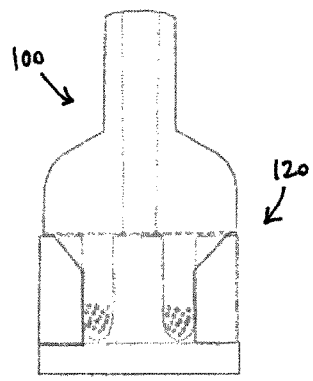
Figure 2C:
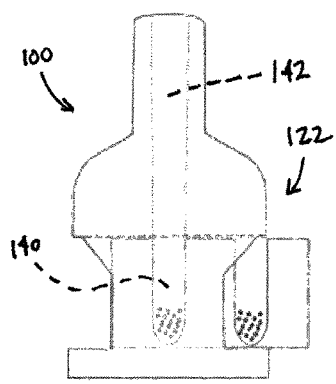
Figure 2D:
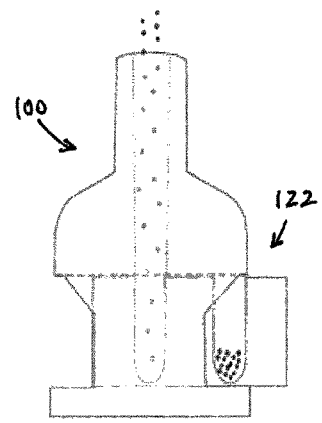
Figure 2E:
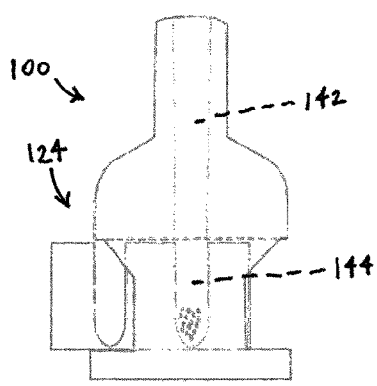
Figure 2F:
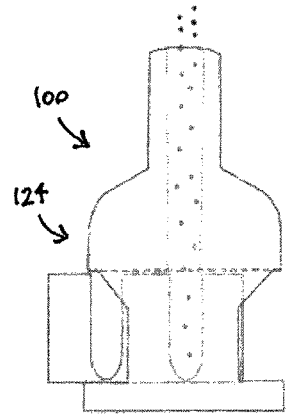

| | | | |
|---|---|---|---|
| 7,431,916 B2 | 10/2008 | Nilsson et al. | |
| 7,435,720 B2 | 10/2008 | Quay et al. | |
| 7,516,741 B2 | 4/2009 | Glusker et al. | |
| 7,521,068 B2 | 4/2009 | Bosch et al. | |
| 7,534,914 B2 | 5/2009 | Koike et al. | |
| 7,541,022 B2 | 6/2009 | Staniforth et al. | |
| 7,556,035 B2 | 7/2009 | Young et al. | |
| 7,556,798 B2 | 7/2009 | Edwards et al. | |
| 7,559,325 B2 | 7/2009 | Dunkley et al. | |
| 7,628,978 B2 | 12/2009 | Weers et al. | |
| 7,651,770 B2 | 1/2010 | Berkland et al. | |
| 7,669,596 B2 | 3/2010 | Alston | |
| 7,682,614 B2 | 3/2010 | Strober et al. | |
| 7,744,906 B2 | 6/2010 | Coates | |
| 7,790,145 B2 | 9/2010 | Weers et al. | |
| 7,806,117 B2 | 10/2010 | Tsutsui | |
| 7,878,193 B2 | 2/2011 | Kladders et al. | |
| 7,919,119 B2 | 4/2011 | Straub et al. | |
| 7,954,491 B2 | 6/2011 | Hrkach | |
| 8,069,851 B2 | 12/2011 | Dunkley et al. | |
| 8,075,919 B2 | 12/2011 | Brown et al. | |
| 8,114,438 B2 | 2/2012 | Pipkin et al. | |
| 8,168,223 B1 | 5/2012 | Tarara et al. | |
| 8,173,168 B2 | 5/2012 | Platz et al. | |
| 8,201,555 B2 | 6/2012 | Chawla | |
| 8,236,786 B2 | 8/2012 | Finch et al. | |
| 8,246,934 B2 | 8/2012 | Weers et al. | |
| 8,530,463 B2 | 9/2013 | Cartt et al. | |
| 8,561,609 B2 | 10/2013 | Donovan et al. | |
| 8,623,419 B2 | 1/2014 | Malakhov et al. | |
| 8,771,744 B2 | 7/2014 | Ruecroft et al. | |
| 8,790,648 B2 | 7/2014 | Tocker et al. | |
| 8,795,634 B2 | 8/2014 | Illum et al. | |
| 8,940,683 B2 | 1/2015 | Levitt | |
| 8,985,102 B2 | 3/2015 | Hodson et al. | |
| 8,997,799 B2 | 4/2015 | Hodson et al. | |
| 9,051,302 B2 | 6/2015 | Winssinger et al. | |
| 9,061,352 B2 | 6/2015 | Lipp et al. | |
| 9,085,632 B2 | 7/2015 | Coates et al. | |
| 9,101,539 B2 | 8/2015 | Nagata et al. | |
| 9,125,999 B2 | 9/2015 | Rolfs et al. | |
| 9,138,407 B2 | 9/2015 | Caponetti et al. | |
| 9,492,413 B2 | 11/2016 | Ludwig et al. | |
| 9,757,395 B2* | 9/2017 | Yadidi | A61K 31/616 |
| 9,757,529 B2* | 9/2017 | Yadidi | A61K 31/616 |
| 9,993,488 B2* | 6/2018 | Yadidi | A61K 31/616 |
| 2002/0025917 A1 | 2/2002 | Pappalardo | |
| 2003/0176421 A1 | 9/2003 | Watson et al. | |
| 2003/0186843 A1 | 10/2003 | Staniforth et al. | |
| 2003/0232019 A1 | 12/2003 | Basu et al. | |
| 2004/0049022 A1 | 3/2004 | Nyce et al. | |
| 2004/0092470 A1 | 5/2004 | Staniforth et al. | |
| 2004/0105821 A1 | 6/2004 | Bernstein et al. | |
| 2004/0206350 A1 | 10/2004 | Alston et al. | |
| 2005/0000518 A1 | 1/2005 | Dunkley et al. | |
| 2005/0004079 A1 | 1/2005 | Benjamin et al. | |
| 2005/0084528 A1 | 4/2005 | Saeed et al. | |
| 2005/0148555 A1 | 7/2005 | Gupta et al. | |
| 2005/0180926 A1 | 8/2005 | Lecourt et al. | |
| 2005/0249697 A1 | 11/2005 | Uhrich et al. | |
| 2006/0002995 A1 | 1/2006 | Harwigsson | |
| 2006/0030550 A1 | 2/2006 | Lithgow et al. | |
| 2006/0257987 A1 | 11/2006 | Gonzalez Valcarcel et al. | |
| 2006/0293217 A1 | 12/2006 | Barker et al. | |
| 2007/0021382 A1 | 1/2007 | Assaf et al. | |
| 2007/0072939 A1 | 3/2007 | Kupper | |
| 2007/0116761 A1 | 5/2007 | Desai et al. | |
| 2007/0123571 A1 | 5/2007 | Raj et al. | |
| 2007/0178166 A1 | 8/2007 | Bernstein et al. | |
| 2007/0232575 A1 | 10/2007 | Baulieu et al. | |
| 2008/0066741 A1 | 3/2008 | Lemajieu et al. | |
| 2008/0127972 A1* | 6/2008 | Morton | A61K 9/0075 128/203.15 |
| 2008/0226736 A1 | 9/2008 | Caponetti et al. | |
| 2008/0306033 A1* | 12/2008 | Franzone | A61K 31/196 514/159 |
| 2009/0011030 A1 | 1/2009 | Jouhikainen et al. | |
| 2009/0110679 A1 | 4/2009 | Li et al. | |
| 2009/0136561 A1 | 5/2009 | Von Rechenberg et al. | |
| 2009/0220435 A1 | 9/2009 | Quay et al. | |
| 2009/0308392 A1 | 12/2009 | Smutney et al. | |
| 2009/0312380 A1 | 12/2009 | Becker | |
| 2010/0132705 A1 | 6/2010 | De Vos | |
| 2010/0158819 A1 | 6/2010 | Kligerman et al. | |
| 2010/0168710 A1 | 7/2010 | Braithwaite | |
| 2010/0234442 A1 | 9/2010 | Duarte-Vazquez et al. | |
| 2010/0242960 A1 | 9/2010 | Zangerle | |
| 2010/0258118 A1 | 10/2010 | Morton | |
| 2010/0316724 A1 | 12/2010 | Whitfield et al. | |
| 2010/0319694 A1 | 12/2010 | Cook et al. | |
| 2011/0112134 A1 | 5/2011 | Hutchinson et al. | |
| 2011/0142914 A1 | 6/2011 | Persaud et al. | |
| 2011/0146678 A1 | 6/2011 | Ruecroft et al. | |
| 2011/0166133 A1 | 7/2011 | Albaugh et al. | |
| 2011/0189106 A1 | 8/2011 | Danzig et al. | |
| 2011/0250130 A1 | 10/2011 | Benatuil et al. | |
| 2011/0263610 A1 | 10/2011 | Wan et al. | |
| 2011/0277752 A1 | 11/2011 | Cheu et al. | |
| 2012/0017892 A1 | 1/2012 | Ludwig | |
| 2012/0046251 A1 | 2/2012 | Schaefer et al. | |
| 2012/0064126 A1* | 3/2012 | Sung | A61K 9/0075 424/400 |
| 2012/0125325 A1 | 5/2012 | Bannister et al. | |
| 2012/0132203 A1 | 5/2012 | Hodson et al. | |
| 2012/0135055 A1* | 5/2012 | Mcaffer | A61K 9/0075 424/400 |
| 2012/0145150 A1* | 6/2012 | Donovan | A61M 16/127 128/203.15 |
| 2012/0152245 A1 | 6/2012 | Rolfs et al. | |
| 2012/0263680 A1 | 10/2012 | Lander et al. | |
| 2012/0276193 A1 | 11/2012 | Graversen et al. | |
| 2012/0291780 A1 | 11/2012 | Donovan et al. | |
| 2012/0308566 A1 | 12/2012 | Martin et al. | |
| 2012/0309809 A1 | 12/2012 | Green et al. | |
| 2013/0004969 A1 | 1/2013 | Peschon et al. | |
| 2013/0028942 A1 | 1/2013 | Surber et al. | |
| 2013/0316001 A1 | 11/2013 | Popov et al. | |
| 2014/0065219 A1 | 3/2014 | Bosch et al. | |
| 2014/0079784 A1 | 3/2014 | Burnier et al. | |
| 2014/0174437 A1 | 6/2014 | Yadidi | |
| 2014/0174440 A1 | 6/2014 | Yadidi | |
| 2014/0213560 A1 | 7/2014 | Vakkalanka | |
| 2014/0234330 A1 | 8/2014 | Budelsky et al. | |
| 2014/0239525 A1 | 8/2014 | McConville et al. | |
| 2014/0242174 A1 | 8/2014 | Walker | |
| 2014/0322238 A1 | 10/2014 | Budelsky et al. | |
| 2014/0322328 A1 | 10/2014 | Yadidi | |
| 2014/0364837 A1 | 12/2014 | Boyes et al. | |
| 2015/0005230 A1 | 1/2015 | Eliasof | |
| 2015/0045332 A1 | 2/2015 | Swenson | |
| 2015/0050713 A1 | 2/2015 | Malakhov et al. | |
| 2015/0059746 A1 | 3/2015 | Green | |
| 2015/0093338 A1 | 4/2015 | Farber | |
| 2015/0132386 A1 | 5/2015 | Heng et al. | |
| 2015/0136130 A1 | 5/2015 | Dehaan et al. | |
| 2015/0224129 A1 | 8/2015 | Trottein et al. | |
| 2015/0239866 A1 | 8/2015 | Machacek et al. | |
| 2015/0239966 A1 | 8/2015 | Baciu et al. | |
| 2015/0239987 A1 | 8/2015 | Liang et al. | |
| 2015/0284381 A1 | 10/2015 | Andresen et al. | |
| 2015/0320694 A1 | 11/2015 | Gu et al. | |
| 2015/0322070 A1 | 11/2015 | Rao et al. | |

FOREIGN PATENT DOCUMENTS

| | | |
|---|---|---|
| CN | 102058886 A1 | 5/2011 |
| EP | 1177805 A1 | 2/2002 |
| EP | 1177805 A1 | 2/2002 |
| EP | 1238680 A1 | 9/2002 |
| EP | 1350511 A1 | 10/2003 |
| EP | 1814521 A1 | 8/2007 |
| JP | 2003512431 A | 4/2003 |

(56) References Cited

FOREIGN PATENT DOCUMENTS

| JP | 2004509141 A | | 3/2004 | |
|---|---|---|---|---|
| JP | 2008-505126 A | | 2/2008 | |
| WO | WO 9511666 A1 | * | 5/1995 | ............ A61K 9/0075 |
| WO | 2000027359 A1 | | 5/2000 | |
| WO | WO-2000/027359 A1 | | 5/2000 | |
| WO | 2001030353 | | 5/2001 | |
| WO | 2002024158 | | 3/2002 | |
| WO | 2003047598 A1 | | 6/2003 | |
| WO | 2003047628 A1 | | 6/2003 | |
| WO | 2005040163 A1 | | 5/2005 | |
| WO | 2005041886 A2 | | 5/2005 | |
| WO | 2006002549 A1 | | 1/2006 | |
| WO | 2006017354 A1 | | 2/2006 | |
| WO | 2007072503 A2 | | 6/2007 | |
| WO | WO-2012/061902 A1 | | 5/2012 | |
| WO | 2012107364 A1 | | 8/2012 | |
| WO | 2012107765 A2 | | 8/2012 | |
| WO | 2013004999 A1 | | 1/2013 | |
| WO | 2014131851 A1 | | 9/2014 | |
| WO | 2014155103 A1 | | 10/2014 | |
| WO | 2015002703 A1 | | 1/2015 | |
| WO | 2015011244 A1 | | 1/2015 | |
| WO | 2015148415 A2 | | 1/2015 | |
| WO | 2015054574 A1 | | 4/2015 | |
| WO | 2015127315 A1 | | 8/2015 | |
| WO | 2015153838 A1 | | 10/2015 | |
| WO | 2015155544 A1 | | 10/2015 | |

OTHER PUBLICATIONS

Hadinoto, et al., "Drug release study of large hollow nanoparticulate aggregates carrier particles for pulmonary delivery," International Journal of Pharmaceutics, Jul. 24, 2007, vol. 341, No. 1-2, pp. 195-206.
"Aspirin", Martindale: The Complete Drug Reference, 33$^{rd}$ ed., 2002 Pharmaceutical press, pp. 14-18.
Soleti, et al., "Aspirin inhalation treatment for COPD patients: Preliminary studies on PK and inflammatory biomarkers," 136$^{th}$ Annual Meeting of the American Neurological Association, Sep. 25, 2011, Thematic Poster Session P825.
Roth, et al., "Aspirin, Platelets, and Thrombosis: Theory and Practice," Blood, Feb. 15, 1994, vol. 83, No. 4, pp. 885-898.
"Internal Analgesic: Antipyretic, and Antirheumatic Drug Products for Over-The-Counter Human Use: Final Rule for Professional Labeling of Aspirin, Buffered Aspirin, and Aspirin in Combination with Antacid Drug Products," Federal Register, Oct. 23, 1998, vol. 63, No. 205, pp. 56802-56819.
Rocca, et al., "Variability in the Responsiveness to Low-Dose Aspirin: Pharmacological and Disease-Related Mechanisms," Thrombosis, 2012, 11 pages.
Awa, et al., "Prediction of time-dependent interaction of aspirin with ibuprofen using a pharmacokinetic/pharmacodynamics model," Journal of Clinical Pharmacy and Therapeutics, 2012, vol. 37, pp. 469-474.
Kim, et al., "Airway Responsiveness to Inhaled Aspirin is Influenced by Airway Hyperresponsiveness in Asthmatic Patients," The Korean Journal of Internal Medicine, Sep. 2010, vol. 25, No. 3, pp. 309-316.
International Search Report dated Dec. 10, 2013 from Corresponding PCT Application No. PCT/US2013/051895.
International Preliminary Examination Report dated Dec. 10, 2013 from Corresponding PCT Application No. PCT/US2013/051895.
Geller, et al., "Development of an Inhaled Dry-Powder Formulation of Tobramycin Using PlumoSphere Technology," J Aerosol Med Pulm Drug Deliv, Aug. 2011, 24(4), pp. 175-182.

Hovione—Particle Design Technologies, <http://www.hovione.com/pd/particledesigntechnologies.asp>, visited Aug. 2013.
Hovione TwinCaps Dry Powder Inhaler, <http://www.hovione.com/twincaps/twincaps.asp>, visited Aug. 2013.
Phillips et al., "Inhaled lysine-aspirin as a bronchoprovocation procedure in aspirin-sensitive asthma: its repeatability, absence of a late-phase reaction, and the role of histamine," J Allergy Clin Immunol, Aug. 1989; 84(2):232-41.
Press release by Activaero GmbH, Dec. 19, 2006, <http://www.pharmaloco.com/news_detail/Activaero+and+Group+of+Resaerchers+Receive+Grant+for+Develop/14009/index.html>.
Sestini et al., "Different Effects of Inhaled Aspirin-like Drugs on Allergen-Induced Early and Late Asthmatic Responses," Am J Respir Crit Care Med, Apr. 1, 1999 vol. 159 No. 4 1228-1233.
Sestini, et al., "Protective effect of inhaled lysine acetylsalicylate on allergen-induced early and late asthmatic reactions," J Allergy Clin Immunol, 1997 vol. 100, pp. 71-77.
Iwamoto, "Gastrointestinal and Hepatic First-Pass Metabolism of Aspirin in Rats," J Pharm Pharmacol. Mar. 1982; 34(3), pp. 176-180.
Jaffe, et al., "Recovery of Endothelial Cell Prostacyclin Production after Inhibition by Low Doses of Aspirin," The American Society for Clinical Investigation, Inc., Mar. 1979, vol. 63, pp. 532-535.
"Physicians' Health Study I," <http://phs.bwh.harvard.edu/phs1.htm>, Mar. 2009.
ATT Collaboration, "Aspirin in the Primary and Secondary Prevention of Vascular Disease: Collaborative Meta-Analysis of Individual Participant Data from Randomised Trials," The Lancet, 2009, 373:1849-1860.
Kurth, et al., "Inhibition of Clinical Benefits of Aspirin on First Myocardial Infarction by Nonsteroidal Antiinflammatory Drugs," Circulation, 2003, 108:1191-1195.
Christen, et al., "Low-dose Aspirin and Risk of Cataract and Subtypes in a Randomized Trial of U.S. Physicians" Ophthalmic Epidemiology, 1998, vol. 5, No. 3, pp. 133-142.
The Dutch TIA Trial Study Group, "A Comparison of Two Doses of Aspirin (30 mg vs. 283 mg a day) in Patients After a Transient Ischemic Attack or Minor Ischemic Stroke," The New England Journal of Medicine, 1991, vol. 325, No. 18, pp. 1261-1266.
Boysen, et al., "Danish Very-low-dose Aspirin After Carotid Endarterectomy Trial," Stroke, 1988, 19:1211-1215.
Algra, et al., "Aspirin at Any Dose Above 30 mg Offers Only Modest Protection After Cerebral Ischaemia," J of Neurology, Neurosurgery & Psychiatry, 1996, 60:197-199.
Chew, et al., "The Role of Particle Properties in Pharmaceutical Powder Inhalation Formulations," Journal of Aerosol Medicine, 2002, vol. 15, No. 3, pp. 325-330.
Sung, et al., "Nanoparticles for Drug Delivery to the Lungs," Trends in Biotechnology, 2007, vol. 25, No. 12.
Asprin Dosage-Drugs, www.druigs.com, Dec. 2011.
Hadinoto, et al. "Drug Release Study of Large Hollow Nanoparticulate Aggregates Carrier Particles for Pulmonary Delivery", International Journal of Pharmaceutics (2007), 341(1-2), 195-206.
Kupczyk, et al. "Lipoxin A4 Generation Is Decreased in Aspirin-Sensitive Patients in Lysine-Aspirin Nasal Challenge in Vivo Model", Allergy (Oxford, United Kingdom) (2009), 64(12), 1746-1752.
State Intellectual Property Office PRC China, First Office Action for Chinese Application No. 201380077562X, with English translation, dated Jul. 17, 2017, 14 pgs.
Japanese Patent Office , "Office Action", for Japanese Patent Application No. 2016-511717, with English translation, dated Apr. 11, 2017, 7 pgs.
European Patent Office , "Examination Report", for European Application No. 13745533.3, dated Nov. 6, 2017, 6 pgs.
Japanese Patent Office , "Notice of Reasons for Refusal" with English translation, for Japanese Application No. 2016/511717, dated Oct. 31, 2017, 9 pgs.

* cited by examiner

DRY POWDER FORMULATIONS AND METHODS OF USE

CROSS REFERENCE TO RELATED APPLICATIONS

This application claims the benefit of U.S. Provisional Application No. 61/817,435, filed Apr. 30, 2013, which is incorporated by reference in its entirety.

FIELD

The subject technology relates generally to pulmonary delivery of NSAIDs, such as aspirin. The subject technology also relates generally to apparatuses and methods for delivery of substances, e.g., delivery of medication to the lungs using by inhalation for treating disease.

BACKGROUND

Pulmonary delivery of therapeutic agents can offer several advantages over other modes of delivery. These advantages include rapid onset, the convenience of patient self-administration, the potential for reduced drug side-effects, ease of delivery by inhalation, the elimination of needles, and the like. Inhalation therapy is capable of providing a drug delivery system that is easy to use in an inpatient or outpatient setting, results in very rapid onset of drug action, and produces minimal side effects.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include relatively large primary liquid aerosol droplet size often requiring impaction of the primary droplet onto a baffle to generate secondary splash droplets of respirable sizes, lack of liquid aerosol droplet size uniformity, significant recirculation of the bulk drug solution, and low densities of small respirable liquid aerosol droplets in the inhaled air. In addition, a particular compound of interest may not be compatible with solvents typically used in nebulizer delivery systems.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved, however the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. No. 6,131,570; U.S. Pat. No. 5,724,957; and U.S. Pat. No. 6,098,620. Disadvantages of this technique include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 6,921,6527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability, which considerably diminish dispersibility and the efficiency of dry powder-based inhalation therapies. For example, interparticular Van der Waals interactions and capillary condensation effects are known to contribute to aggregation of dry particles. Hickey, A. et al., "Factors Influencing the Dispersion of Dry Powders as Aerosols", Pharmaceutical Technology, August, 1994.

To overcome interparticle adhesive forces, Batycky et al. in U.S. Pat. No. 7,182,961 teach production of so called "aerodynamically light respirable particles," which have a volume median geometric diameter (VMGD) of greater than 5 microns ($\mu$m) as measured using a laser diffraction instrument such as HELOS (manufactured by Sympatec, Princeton, N.J.). See Batycky et al., column 7, lines 42-65. Another approach to improve dispersibility of respirable particles of average particle size of less than 10 $\mu$m, involves the addition of a water soluble polypeptide or addition of suitable excipients (including amino acid excipients such as leucine) in an amount of 50% to 99.9% by weight of the total composition. Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No. 6,737,044 to Dickinson et al., U.S. Pat. No. 6,546,928 to Ashurst et al., or U.S. Pat. Applications 20090208582 to Johnston et al.

A further limitation that is shared by each of the above methods is that the aerosols produced typically include substantial quantities of inert carriers, solvents, emulsifiers, propellants, and other non-drug material. In general, the large quantities of non-drug material are required for effective formation of respirable dry particles small enough for alveolar delivery (e.g. less than 5 µm and preferably less than 3 µm). However, these amounts of non-drug material also serve to reduce the purity and amount of active drug substance that can be delivered. Thus, these methods remain substantially incapable of introducing large active drug dosages accurately to a patient for systemic delivery.

A thromboembolic event, such as myocardial infarction, deep venous thrombosis, pulmonary embolism, thrombotic stroke, etc., can present with certain symptoms that allow a patient or clinician to provide an initial therapy or treatment for the event. In some situations, an 81 mg, low dose, or baby aspirin or a regular aspirin (330 mg) may be orally administered in order to provide an initial treatment for the patient.

There remains a need for providing novel formulations of non-steroidal anti-inflammatory drugs ("NSAIDs"), such as aspirin, that are suitable for pulmonary delivery.

SUMMARY

The subject technology generally relates to respirable dry powders comprising dry particles that comprise an NSAID, such as acetylsalicylic acid, as an active ingredient. The respirable dry particles may be large or small, e.g., a geometric diameter (VMGD) between 0.5 µm and 30 µm. Alternatively or in addition, the respirable dry powders can have a mass median aerodynamic diameter (MMAD) of about 20 μm or less. Optionally, the MMAD of the particles may be between 0.5 and 10 μm, more preferably between 1 and 10 μm.

The dry powders may also comprise a mixture of particles of large sizes (e.g., 20-30 μm) and of small sizes (e.g., 5 μm or less). This way, smaller particles could reach the lower respiratory tract and larger particles would be captured in the upper respiratory tract.

The respirable dry powder compositions can include a pharmaceutically acceptable excipient, such as leucine, sodium citrate, maltodextrin or mannitol, which may be present in an amount of about 5% to about 90% or by weight. The inclusion of an excipient is optional.

In some embodiments, the NSAID, such as acetylsalicylic acid, is provided in a dry powder formulation comprising a mixture of particles of various sizes, for example, a mixture of (i) particles having a mean geometric diameter (VMGD) and/or mass median aerodynamic diameter (MMAD) of 5 μm or less, and (ii) particles having a mean geometric diameter (VMGD) and/or mass median aerodynamic diameter (MMAD) of 15 μm or greater. In some embodiments the composition may further include a pharmaceutically acceptable excipient. In other embodiments, the composition is free or substantially free of excipient. In certain embodiments, the composition is free or substantially free of anti-aggregation excipient.

The subject technology also relates to a respirable dry powder or dry particle, as described herein, for use in therapy (e.g., treatment, prophylaxis, or diagnosis). The subject technology also relates to the use of a respirable dry particle or dry powder, as described herein, for use in treatment (including prophylactic treatment, such as prevention or reducing the risk) of a cardiovascular disease (such as thrombosis) as described herein, and in the manufacture of a medicament for the treatment, prophylaxis or diagnosis of a cardiovascular disease (such as thrombosis) as described herein.

The subject technology also provides a drug delivery system for treating (including prophylactic treatment or reducing the risk of) a cardiovascular disease (such as thrombosis), the system comprising: a therapeutically effective dose of an NSAID (such as acetylsalicylic acid) in dry powder form; a dry powder inhaler, the dry powder inhaler comprising a mouthpiece, a reservoir for receiving the dose of the NSAID (such as acetylsalicylic acid), and an actuation member for making available the dose of the acetylsalicylic acid for inhalation by the patient through the mouthpiece. Preferably, the dose of the NSAID (such as acetylsalicylic acid) is about 40 mg or less, more preferably, 30 mg or less.

Another aspect of at least one embodiment disclosed herein includes the recognition of a need for improved apparatuses and methods for delivery of drugs for treating disease that utilize a dosage that is effective to reduce a risk of a thromboembolic event in a patient, lower than traditional dosages, and administered using a more direct delivery mechanism to the systemic blood stream.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 1 is a schematic view of a patient using a dry powder inhaler, in accordance with some implementations of the methods and systems disclosed herein.

FIGS. 2A-F illustrate usages and a configuration of a dry powder inhaler, according to some embodiments.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

1. Introduction

Thromboembolic Symptoms and Events

A thromboembolic event, such as myocardial infarction, deep venous thrombosis, pulmonary embolism, thrombotic stroke, etc., can present with certain symptoms that allow a patient or clinician to provide an initial therapy or treatment for the event. In some situations, an 81 mg, low dose, or baby aspirin or a regular aspirin (330 mg) may be orally administered in order to provide an initial treatment for the patient.

According to some embodiments disclosed herein is the realization that this treatment may not act as quickly as necessary to provide a sufficient therapeutic effect and therefore, may lead to a less preferred outcome. Thus, in some embodiments, a drug delivery system and related methods are disclosed that provide an accelerated and more efficient pathway and treatment for reducing the risk of a thromboembolic event and/or providing treatment for a thromboembolic event. For example, some embodiments provide systems and methods of administering a non-steroidal anti-inflammatory drug ("NSAID") by inhalation, such as by a dry powder inhaler ("DPI") or a metered dose inhaler ("MDI").

Delivery Mechanisms for Drugs

Drugs can be administered orally in different ways, such as liquids, capsules, tablets, or chewable tablets. The oral route is used most often because it is the most convenient, safest, and least expensive. However, oral drug delivery has limitations because of the way a drug typically moves through the digestive tract.

For example, when a drug is administered orally, it is absorbed in the mouth, stomach, and the small intestine. Before the drug enters the bloodstream, it must pass through the intestinal wall and travels to the liver. While passing through the intestinal wall and liver, the drug is metabolized, which can decrease the amount of the drug that actually reaches the bloodstream. The metabolism of the drug reduces the bioavailability of the drug and is often termed the "first pass effect." The fraction of the drug lost during due to the first pass effect is generally determined by absorption in the liver and gut wall, and gastrointestinal lumen enzymes, gut wall enzymes, bacterial enzymes, and hepatic (liver) enzymes.

Generally, the first pass effect on aspirin significantly reduces the bioavailability of the administered dosage. For example, due to the acidic conditions in the stomach, aspirin is absorbed in the stomach and the upper small intestine. After being absorbed, aspirin is metabolized to acetic acid and salicylate. When taken orally, generally only about one to two-thirds of the dose of aspirin is bioavailable due to the first pass effect.

For example, in Iwamoto K., GASTROINTESTINAL AND HEPATIC FIRST-PASS METABOLISM OF ASPIRIN IN RATS, J Pharm Pharmacol. 1982 March; 34(3), pp. 176-80, the study examines the absorption of aspirin in four male subjects following an oral solution of 650 mg. As stated in the study report, "the absorption process appeared to follow first-order kinetics, with a half-life ranging from 4.5 to 16.0 min. between subjects. Comparison of the area under the aspirin plasma concentration-time curve following intravenous and oral routes indicated that only 68% of the dose reached the peripheral circulation intact."

Applicant has determined that even drugs that are administered by inhalation undergo a first pass effect. For drug administration by inhalation, smaller particles proceed via a nasal route, down the windpipe (trachea) and into the lungs. The size of the particles can be determinative of the overall efficacy of the treatment. Once inside the lungs, these particles are absorbed into the bloodstream.

Few drugs are administered by inhalation because the dosage of an inhaled drug, as well as the delivery timing, can often be difficult to measure. Usually, this method is used to administer drugs that act specifically on the lungs, such as aerosolized antiasthmatic drugs in metered-dose containers, and to administer gases used for general anesthesia.

Pharmacokinetics of Aspirin

Aspirin is the acetylated form of salicylic acid, and the active chemical in aspirin is called acetylsalicylic acid (ASA). Aspirin is used by millions of people to achieve desirable effects, and by many people, baby aspirin is often used daily. The principal effect of aspirin is to impair the function of cyclooxygenase enzymes (specifically, COX1 and COX2 enzymes).

By inhibiting COX1, aspirin can irreversibly inhibit platelet aggregation, which decreases the risk of blood clots. Additionally, the impairment of the COX2 enzyme can reduce inflammation, stiffness, and pain in the body by inhibiting prostaglandins and thromboxanes. As such, individuals at high risk for heart attack, stroke, or with inflammation often take aspirin to address symptoms and effects of these conditions. As noted, aspirin can effectively reduce the likelihood of such myocardial events and reduce pain and inflammation with a dose as small as a baby aspirin. However, due at least in part to its inhibition of COX1, aspirin can increase the risk of bleeding and cause damage to organs such as the stomach and intestines, which can be painful.

Dry Powder Inhaler Technology

As stated above, the oral delivery of aspirin may create a risk of damage to the stomach wall leading to pain, indigestion and a high risk of bleeding. Further, according to at least one of the aspects of embodiments disclosed herein is the realization that it is often difficult to orally administer a drug during emergency situations that may implicate or result in a thromboembolic event. For example, the patient may be experiencing vomiting or otherwise be unable to take the drug orally. Additionally, oral administration of a drug may be undesirable because the drug does not reach the systemic blood stream immediately, thus delaying the important effects of the drug. Even so, due to the first pass effect in the liver and gut, the amount of drug reaching systemic circulation is much less than that administered. Therefore, according to aspects of various embodiments disclosed herein is the realization that an alternative route of administration could avoid these unwanted side-effects.

Various embodiments disclosed herein reflect the novel realization that delivery of a drug by inhalation in the early stages of an emergency situation can provide a fast-acting, effective form of preliminary treatment of certain medical conditions. For example, in some embodiments, upon receiving a complaint of a symptom of a serious thromboembolic event, a patient can be administered, by DPI, a therapeutic amount of a NSAID. The NSAID can address problems associated with or provide an initial treatment for the medical condition.

However, dry powder inhalation of drugs has generally been limited by cough, to dosages of less than a milligram. Recent developments in particle engineering, in particular the development of PulmoSphere™ technology, have enabled the delivery of a larger amount of dry powder to the lungs in a single actuation. See David E. Geller, M. D., et al., DEVELOPMENT OF AN INHALED DRY-POWDER FORMULATION OF TOBRAMYCIN USING PULMOSPHERE™ TECHNOLOGY, J Aerosol Med Pulm Drug Deliv. 2011 August; 24(4), pp. 175-82. In this publication, a dose of 112 mg tobramycin (in four capsules) was effectively delivered via PulmoSpheres™.

In accordance with some embodiments is the realization that the body includes various particle filters that limit the efficacy of inhaled drugs. For example, the oropharynx tends to prevent passage of particles having a diameter greater than 5 μm. However, in order to reach the alveoli, particles must have a size from about 1 μm to about 5 μm. Accordingly, some embodiments herein disclose the preparation and use of inhalable aspirin using technology similar to PulmoSpheres™ to produce particles with a median geometric diameter of from about 1 μm to about 5 μm, and in some embodiments, from about 1.7 μm to about 2.7 μm.

There has been no single dose use of aspirin by dry powder inhaler to replace the traditional daily use of a NSAID (such as a baby aspirin) or emergency use of a NSAID as preventative care for symptoms of a thromboembolic event. Accordingly, some embodiments disclosed herein provide methods for administering a NSAID by dry powder inhalation in an amount less than the dosage of a baby aspirin (e.g., less than 81 mg).

Therefore, in some embodiments, a method for treating disease, e.g., by reducing the risk of a thromboembolic event, can be provided, which comprises administering a NSAID, such as a salicylate, by a DPI or MDI. For example, the method can comprise administering acetylsalicylic acid by a DPI or MDI. The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, according to some embodiments, the dosage can be from about 2 mg to about 30 mg of acetylsalicylic acid. In some embodiments, the dosage can be from about 4 mg to about 25 mg of acetylsalicylic acid. The dosage can be from about 6 mg to about 20 mg of acetylsalicylic acid. Further, in some embodiments, the dosage can be from about 8 mg to about 15 mg of acetylsalicylic acid. Further, in some embodiments, the dosage can be from about 10 mg to about 13 mg of acetylsalicylic acid. For example, in some embodiments, the dosage can be about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg of acetylsalicylic acid.

Additionally, the dose of acetylsalicylic acid can be less than about 80 mg. In some embodiments, the dose of acetylsalicylic acid can be from about 1 mg to about 75 mg. In some embodiments, the dose of acetylsalicylic acid can be from about 2 mg to about 60 mg. In some embodiments, the dose of acetylsalicylic acid can be from about 5 mg to about 40 mg. In some embodiments, the dose of acetylsalicylic acid can be from about 10 mg to about 30 mg. In some embodiments, the dose of acetylsalicylic acid can be from about 12 mg to about 25 mg. In some embodiments, the dose of acetylsalicylic acid can be from about 15 mg to about 20 mg.

In accordance with some embodiments, such dosages can provide a bioequivalent dosage when compared to typical dosages of 81 mg to about 325 mg, while demonstrating few negative side effects.

Thus, in some embodiments, a NSAID, such as aspirin, can be administered by DPI or MDI in a single dose that is much less than a traditional oral dose of aspirin, which can provide a bioequivalent treatment while tending to avoid the negative side effects associated with some NSAIDs, such as aspirin. Further, systems of administering such treatments are also provided.

The DPI or MDI can have a mouthpiece and an actuation member for making available the NSAID for inhalation by a patient to reduce the risk of the thromboembolic event.

For example, according to some embodiments, a method of reducing the risk of a thromboembolic event is provided and can comprise administering a dose of a non-steroidal anti-inflammatory drug by a dry powder inhaler. The dose can be effective to reduce a risk of a thromboembolic event in a patient. The dry powder inhaler can have a mouthpiece and an actuation member for making available the dose of the non-steroidal anti-inflammatory drug for inhalation by the patient to reduce the risk of the thromboembolic event.

A drug delivery system can also be provided according to some embodiments, for treating a disease, for example, by reducing the risk of a thromboembolic event. The system can comprise a dose of a non-steroidal anti-inflammatory drug in powder form. The dose can be effective to reduce a risk of a thromboembolic event in a patient. The system can also comprise a dry powder inhaler. The dry powder inhaler can have a mouthpiece, a reservoir for receiving the dose of the non-steroidal anti-inflammatory drug, and an actuation member for making available the dose of the non-steroidal anti-inflammatory drug for inhalation by the patient through the mouthpiece.

In some embodiments, the thromboembolic event comprises at least one of myocardial infarction, deep venous thrombosis, pulmonary embolism, or thrombotic stroke. The dose of the non-steroidal anti-inflammatory drug can be administered as a preliminary treatment in response to a symptom of a thromboembolic event. The non-steroidal anti-inflammatory drug can comprise aspirin. Further, the dose of the non-steroidal anti-inflammatory drug can be administered in a single dose.

2. Definitions

The term "about", as used here, refers to +/−5% of a value.

The term "dry powder" as used herein refers to a composition contains finely dispersed respirable dry particles that are capable of being dispersed in an inhalation device and subsequently inhaled by a subject. Such dry powder or dry particle may contain up to about 15% water or other solvent, or be substantially free of water or other solvent, or be anhydrous.

The term "dry particles" as used herein refers to respirable particles that may contain up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 μm, preferably about 5 μm or less.

As used herein, the terms "administration" or "administering" of respirable dry particles refers to introducing respirable dry particles to the respiratory tract of a subject.

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "¼ bar," and "0.5/4 bar," respectively, and dispersibility correlates with a low quotient. For example, ¼ bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a ¼ bar or 0.5/4 bar ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by the subject. Dispersibility can also be assessed by measuring the size emitted from an inhaler as a function of flowrate.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia Convention, Rockville, Md., $13^{th}$ Revision, 222-225, 2007. This method utilizes an in vitro device set up to mimic patient dosing.

The terms "FPF(<5.6)," "FPF(<5.6 μm)," and "fine particle fraction of less than 5.6 μm" as used herein, refer to the fraction of a sample of dry particles that have an aerodynamic diameter of less than 5.6 μm. For example, FPF(<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD(<5.6)," where TD means total dose. A similar measurement can be conducted using an eight-stage ACL The eight-stage ACI cutoffs are different at the standard 60 L/min flowrate, but the FPF_TD(<5.6) can be extrapolated from the eight-stage complete data set. The eight-stage ACI result can also be calculated by the USP method of using the dose collected in the ACI instead of what was in the capsule to determine FPF.

The terms "FPF(<3.4)," "FPF(<3.4 μm)," and "fine particle fraction of less than 3.4 μm" as used herein, refer to the fraction of a mass of respirable dry particles that have an aerodynamic diameter of less than 3.4 For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD(<3.4)," where TD means total dose. A similar measurement can be conducted using an eight-stage ACI. The eight-stage ACI result can also be calculated by the USP method of using the dose collected in the ACI instead of what was in the capsule to determine FPF.

The terms "FPF(<5.0)," "FPF(<5.0 μm)," and "fine particle fraction of less than 5.0 μm" as used herein, refer to the fraction of a mass of respirable dry particles that have an aerodynamic diameter of less than 5.0 For example, FPF (<5.0) can be determined by using an eight-stage ACI at the standard 60 L/min flowrate by extrapolating from the eight-stage complete data set. This parameter may also be identified as "FPF_TD(<5.0)," where TD means total dose.

The term "nanoparticles" refers to particles that have a single crystallite grain between about 1 nm to about 900 nm, preferably between about 5 nm to about 500 nm. Individual grains can agglomerate into clusters/agglomerates.

The term "excipient" refers to a pharmacologically inactive substance formulated with the active ingredient ("API") of a medication.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

3. Non-Steroidal Anti-Inflammatory Drugs (NSAIDs)

NSAIDs, such as aspirin, can provide various beneficial effects and contribute to reducing the risk of a cardiovascular disease (such as thrombosis). However, the use of NSAIDs, such as aspirin, in a clinical setting has traditionally been limited to oral administration. Oral administration of aspirin, for example, can result in the loss or inactivation of approximately ⅔ of the oral dosage due to the first pass effect in the gut and liver. While one third of the dosage reaches the systemic blood stream and provides the desired effect, the negative side effects created by the full dosage often deter patients from using aspirin on a regular or daily basis.

Further, in many situations, such as in emergencies, oral administration of NSAIDs, such as aspirin, may be inappropriate because it may take too long to be effective. According to at least one aspect of some embodiments disclosed herein is the realization that an alternative administration method and systems can be implemented that utilize a lower dosage and provide a more direct delivery mechanism to the systemic blood stream. Thus, some embodiments disclosed herein allow for the beneficial effects of NSAIDs, such as aspirin, to be achieved on a regular basis and in emergency situations, while minimizing previous drawbacks associated with the use of NSAIDs.

Various studies have determined that aspirin has a significant effect on reducing the risk of myocardial infarction. However, these studies presented inconclusive data on strokes, pulmonary embolism, or deep venous thrombosis.

These studies have used aspirin dosages of 325 mg. However, these studies have based their findings on oral administration of aspirin and have not suggested DPI or MDI pathways, which are provided in some embodiments disclosed herein. Further, the administration of aspirin has negative side effects, such as significantly increasing major gastrointestinal and extracranial bleeds by over 50%. This has led some to argue that for preventative treatment, aspirin is of uncertain net value.

Further studies have tested whether the benefits of aspirin could be obtained at low dosages, such as that of baby aspirin (i.e., 81 mg). The Swedish Aspirin Low-dose Trial (SALT) found that a low dose (75 mg/day) of aspirin significantly reduces the risk of stroke or death in patients with cerebrovascular ischaemic events. However, the study also reported gastrointestinal side-effects that included a significant excess of bleeding episodes. A Danish study found that patients receiving aspirin as an antithrombotic agent achieved satisfactory platelet inhibition with 50 mg/day, while the remainder of the patients needed over 50 mg/day. Furthermore, a Dutch TIA Study concluded that aspirin at any dose above 30 mg daily prevents 13% of vascular events, and that there is a need for more efficacious drugs. However, no study or teaching has been provided regarding the administration of aspirin by DPI or MDI at very low doses.

Although inhaled dry powder formulations of aspirin have been developed, reports have stated that the formulation was not clinically feasible because it is difficult to meet the high dosage requirements of aspirin (~80 mg/day for low-dose prevention of coronary events and stroke, and at least 300 mg/day for pain or fever relief) via pulmonary delivery of dry powders.

In addition, these reports recognize that adverse effects of dry powder on the lungs, such as coughing, cannot be avoided unless the doses are less than a few tenths of a milligram in a single breath. Thus, prior teachings suggest that higher dosage requirements of aspirin would be impossible to meet using DPI. Finally, some have taught that there is a higher incidence of aspirin intolerance in asthmatic patients when aspirin is delivered by inhalation than orally.

In yet another study, the authors noted that use of nanoparticulate drugs for dry powder inhaler (DPI) delivery is not straightforward. Direct inhalation of nanoparticulate drugs was infeasible due to their small size. The nanometer size leads to the nanoparticulate drugs being predominantly exhaled from the lungs, without any deposition in the lungs taking place. Moreover, a severe aggregation problem arising from the small size makes their physical handling difficult for DPI delivery. Accordingly, "large hollow carrier particles" of nanoparticulate drugs has been developed for pulmonary delivery of some drugs. See Hadinoto et al., *Drug Release Study Of Large Hollow Nanoparticulate Aggregates Carrier Particles For Pulmonary Delivery*, International Journal of Pharmaceutics 341 (2007) 195-20.

In the Hadinoto study, the authors used aspirin as a model for "lowly water-soluble" drugs. The authors acknowledged that "with regard to the aspirin, the nanoparticulate polymer delivery method is not the most suitable method of delivery due to the high dosage requirement of aspirin (~300 mg/day)," and overall, the aim of the study was to identify key facets in the formulation of the large hollow nanoparticulate aggregates. See id.

In some embodiments of the inventions disclosed herein, methods and systems are provided for treating (including prophylactic treatment or reducing the risk of) a disease, for example, treating a cardiovascular disease (such as thrombosis) by administration of a very low amount of a NSAID, such as a low dose of aspirin, by DPI. The dose can be much less than that of a baby aspirin (e.g., less than 81 mg). The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, according to some embodiments, the dosage can be from about 2 mg to about 30 mg. In some embodiments, the dosage can be from about 4 mg to about 25 mg of acetylsalicylic acid. The dosage can be from about 6 mg to about 20 mg of acetylsalicylic acid. Further, in some embodiments, the dosage can be from about 8 mg to about 15 mg of acetylsalicylic acid. Further, in some embodiments, the dosage can be from about 10 mg to about 13 mg of acetylsalicylic acid. For example, in some embodiments, the dosage can be about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg of acetylsalicylic acid.

Additionally, the dose of acetylsalicylic acid can be less than about 80 mg. In some embodiments, the dose of acetylsalicylic acid can be from about 1 mg to about 75 mg. In some embodiments, the dose of acetylsalicylic acid can be from about 2 mg to about 60 mg. In some embodiments, the dose of acetylsalicylic acid can be from about 5 mg to about 40 mg. In some embodiments, the dose of acetylsalicylic acid can be from about 10 mg to about 30 mg. In some embodiments, the dose of acetylsalicylic acid can be from about 12 mg to about 25 mg. In some embodiments, the dose of acetylsalicylic acid can be from about 15 mg to about 20 mg.

Such dosages can provide a bioequivalent dosage when compared to typical dosages of 81 mg to about 325 mg, while demonstrating few negative side effects.

In some embodiments, NSAIDs can be used in various methods and systems. In some embodiments, NSAIDs can include salicylates, i.e., the salts and esters of salicylic acid, which have anti-platelet action. Further, NSAIDs can also include one or more of the following:

Aspirin (Aspirin is a brand name; the chemical is called acetylsalicylic acid)
Celecoxib (Celebrex)
Dexdetoprofen (Keral)
Diclofenac (Voltaren, Cataflam, Voltaren-XR)
Diflunisal (Dolobid)
Etodolac (Lodine, Lodine XL)
Etoricoxib (Algix)
Fenoprofen (Fenopron, Nalfron)
Firocoxib (Equioxx, Previcox)
Flurbiprofen (Urbifen, Ansaid, Flurwood, Froben)
Ibuprofen (Advil, Brufen, Motrin, Nurofen, Medipren, Nuprin)
Indomethacin (Indocin, Indocin SR, Indocin IV)
Ketoprofen (Actron, Orudis, Oruvail, Ketoflam)
Ketorolac (Toradol, Sprix, Toradol IV/IM, Toradol IM)
Licofelone (under development)
Lornoxicam (Xefo)
Loxoprofen (Loxonin, Loxomac, Oxeno)
Lumiracoxib (Prexige)
Meclofenamic acid (Meclomen)
Mefenamic acid (Ponstel)

-continued

Meloxicam (Movalis, Melox, Recoxa, Mobic)
Nabumetone (Relafen)
Naproxen (Aleve, Anaprox, Midol Extended Relief, Naprosyn, Naprelan)
Nimesulide (Sulide, Nimalox, Mesulid)
Oxaporozin (Daypro, Dayrun, Duraprox)
Parecoxib (Dynastat)
Piroxicam (Feldene)
Rofecoxib (Vioxx, Ceoxx, Ceeoxx)
Salsalate (Mono-Gesic, Salflex, Disalcid, Salsitab)
Sulindac (Clinoril)
Tenoxicam (Mobiflex)
Tolfenamic acid (Clotam Rapid, Tufnil)
Valdecoxib (Bextra)

Other alternatives can also be used instead of a NSAID in some methods or systems disclosed herein. Such alternatives include as Plavix (clopidogrel), COX-2 inhibitors, other remedies such as Nattokinase (an enzyme (EC 3.4.21.62, extracted and purified from a Japanese food called nattō). Further, other drugs that provide different beneficial effects, such as being effective to reduce a risk of a cardiovascular disease (such as thrombosis) in a patient, can also be used in some embodiments. Thus, the discussion of methods and systems shall apply generally to these various alternatives, although for discussion purposes, the present disclosure often refers to aspirin. It is contemplated that the methods, effects, pharmacokinetic data, and other considerations relating to aspirin can be equally applied to other NSAIDs, according to some embodiments.

4. Dry Powders and Dry Particles

The subject technology relates to respirable dry powders and dry particles that comprise an NSAID, such as acetylsalicylic acid, as an active ingredient.

In one aspect, the dry particles of the subject technology are small, and preferably are dispersible. The size of the dry particles can be expressed in a variety of ways that are conventional in the art, such as, fine particle fraction (FPF), volumetric median geometric diameter (VMGD), or mass median aerodynamic diameter (MMAD).

In certain embodiments, the dry particles of the subject technology are small and preferably dispersible. For example, the dry particles of the subject technology may have a VMGD as measured by HELOS/RODOS at 1.0 bar of about 10 µm or less (e.g., about 0.1 µm to about 10 µm). Preferably, the dry particles of the subject technology have an VMGD of about 9 µm or less (e.g., about 0.1 µm to about 9 about 8 µm or less (e.g., about 0.1 µm to about 8 µm), about 7 µm or less (e.g., about 0.1 µm to about 7 µm), about 6 µm or less (e.g., about 0.1 µm to about 6 µm), about 5 µm or less (e.g., less than 5 µm, about 0.1 µm to about 5 µm), about 4 µm or less (e.g., 0.1 µm to about 4 µm), about 3 µm or less (e.g., 0.1 µm to about 3 µm), about 2 µm or less (e.g., 0.1 µm to about 2 µm), about 1 µm or less (e.g., 0.1 µm to about 1 µm), about 0.5 µm to about 6 µm, about 0.5 µm to about 5 µm, about 0.5 µm to about 4 µm, about 0.5 µm to about 3 µm, or about 0.5 µm to about 2 µm as measured by HELOS/RODOS at 1.0 bar. In an exemplary embodiment, the dry particles of the subject technology have a VMGD as measured by HELOS/RODOS at 1.0 bar of about 1.3 to about 1.7 µm. In another exemplary embodiment, the dry particles of the subject technology have a VMGD as measured by HELOS/RODOS at 1.0 bar of about 0.5 µm to about 2 µm.

In certain embodiments, the dry particles of the subject technology are large and preferably dispersible. For example, the dry particles of the subject technology may have a VMGD as measured by HELOS/RODOS at 1.0 bar of about 30 µm or less (e.g., about 5 µm to about 30 µm). Preferably, the dry particles of the subject technology have an VMGD of about 25 µm or less (e.g., about 5 µm to about 25 µm), about 20 µm or less (e.g., about 5 µm to about 20 µm), about 15 µm or less (e.g., about 5 µm to about 15 µm), about 12 µm or less (e.g., about 5 prn to about 12 µm), about 10 µm or less (e.g., about 5 µm to about 10 µm), or about 8 µm or less (e.g., 6 µm to about 8 µm) as measured by HELOS/RODOS at 1.0 bar.

The dry powders described herein can comprise a mixture of large particles and small particles.

Preferably, whether the particles are small or large, the dry particles of the subject technology are dispersible, and have ¼ bar and/or 0.5/4 bar of about 2.2 or less (e.g., about 1.0 to about 2.2) or about 2.0 or less (e.g., about 1.0 to about 2.0). Preferably, the dry particles of the subject technology have ¼ bar and/or 0.5/4 bar of about 1.9 or less (e.g., about 1.0 to about 1.9), about 1.8 or less (e.g., about 1.0 to about 1.8), about 1.7 or less (e.g., about 1.0 to about 1.7), about 1.6 or less (e.g., about 1.0 to about 1.6), about 1.5 or less (e.g., about 1.0 to about 1.5), about 1.4 or less (e.g., about 1.0 to about 1.4), about 1.3 or less (e.g., less than 1.3, about 1.0 to about 1.3), about 1.2 or less (e.g., 1.0 to about 1.2), about 1.1 or less (e.g., 1.0 to about 1.1 µm) or the dry particles of the subject technology have ¼ bar of about 1.0.

Alternatively or in addition, the respirable dry particles of the subject technology can have an MMAD of about 10 µm or less, such as an MMAD of about 0.5 µm to about 10 µm. Preferably, the dry particles of the subject technology have an MMAD of about 5 µm or less (e.g. about 0.5 µm to about 5 µm, preferably about 1 µm to about 5 µm), about 4 µm or less (e.g., about 1 µm to about 4 µm), about 3.8 µm or less (e.g. about 1 µm to about 3.8 µm), about 3.5 µm or less (e.g. about 1 µm to about 3.5 µm), about 3.2 µm or less (e.g. about 1 µm to about 3.2 µm), about 3 µm or less (e.g. about 1 µm to about 3.0 µm), about 2.8 µm or less (e.g. about 1 µm to about 2.8 µm), about 2.2 µm or less (e.g. about 1 µm to about 2.2 µm), about 2.0 µm or less (e.g. about 1 µm to about 2.0 µm) or about 1.8 µm or less (e.g. about 1 micron to about 1.8 µm).

Alternatively or in addition, the dry powders and dry particles of the subject technology have a FPF of less than 5.0 µm (FPF_TD<5.0 µm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the subject technology have a FPF of less than 5.0 µm of the emitted dose (FPF_ED<5.0 µm) of at least about 45%, preferably at least about 50%, at least about 60%, at least about 65%, at least about 70%, at least about 75%, at least about 80%, or at least about 85%.

Alternatively or in addition, the respirable dry powders and dry particles of the invention can have an FPF of less than about 5.6 µm (FPF<5.6 µm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention can have an FPF of less than about 3.4 µm (FPF<3.4 µm) of at least about 20%, preferably at least about 25%, at least about 30%, at least about 35%, at least about 40%, at least about 45%, at least about 50%, or at least about 55%.

Alternatively or in addition, the respirable dry powders and dry particles of the subject technology have a tap density of about 0.1 g/cm$^3$ to about 1.0 g/cm$^3$. For example, the small and dispersible dry particles have a tap density of about 0.1 g/cm$^3$ to about 0.9 g/cm$^3$, 0.2 g/cm$^3$ to about 0.9 g/cm$^3$, about 0.2 g/cm$^3$ to about 0.9 g/cm$^3$, about 0.3 g/cm$^3$ to about 0.9 g/cm$^3$, about 0.4 g/cm$^3$ to about 0.9 g/cm$^3$, about 0.5 g/cm$^3$ to about 0.9 g/cm$^3$, or about 0.5 g/cm$^3$ to about 0.8 g/cm$^3$, greater than about 0.4 g/cc, greater than about 0.5 g/cc, greater than about 0.6 g/cc, greater than about 0.7 g/cc, about 0.1 g/cm$^3$ to about 0.8 g/cm$^3$, about 0.1 g/cm$^3$ to about 0.7 g/cm$^3$, about 0.1 g/cm$^3$ to about 0.6 g/cm$^3$, about 0.1 g/cm$^3$ to about 0.5 g/cm$^3$, about 0.1 g/cm$^3$ to about 0.4 g/cm$^3$, about 0.1 g/cm$^3$ to about 0.3 g/cm$^3$, less than 0.3 g/cm$^3$. In a preferred embodiment, tap density is greater than about 0.4 g/cc. In another preferred embodiment, tap density is greater than about 0.5 g/cc. Alternatively, tap density is less than about 0.4 g/cc.

Alternatively or in addition, the respirable dry powders and dry particles of the subject technology can have a water or solvent content of less than about 15% by weight of the respirable dry particle. For example, the respirable dry particles of the subject technology can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the subject technology can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

Depending on the specific applications of the dry powders described herein, the dry powder and particles may contain a low or high percentage of active ingredient in the composition. For example, the dry particles may contain 3% or more, 5% or more, 10% or more, 15% or more, 20% or more, 25% or more, 30% or more, 35% or more, 40% or more, 50% or more, 60% or more, 70% or more, 75% or more, 80% or more, 85%© or more, 90% or more, or 95% or more (weight percentage) of the active ingredient (e.g., acetylsalicylic acid).

5. Delivery of Dry Powders

Through some of the embodiments disclosed herein, Applicants have overcome the challenges acknowledged by prior teachings. In particular, Applicants have recognized that when a drug is inhaled into the lungs, the drug can be dispersed toward the alveoli. Although alveoli primarily function to exchange carbon dioxide for oxygen, alveoli also produce enzymes. Thus, inhaled substances, such as pathogens, drugs, or other chemicals, may be processed at the alveoli.

An alveolus comprises a network of elastic fibers and capillaries, resembling a woven sphere on its outer surface. The capillaries function to carry oxygen depleted blood toward the lungs and oxygen rich blood away from the lungs, via the pulmonary artery and the pulmonary vein. The interior of each alveoli comprises a thin tissue known as an alveolar lining or epithelium. Alveolar epithelium is made of two distinct types of cells, known as flat type I and type II. Flat type I cells cover most of the surface area of the epithelium and are closely spaced, allowing only small molecules to pass therebetween, such as oxygen and carbon dioxide. Type II alveolar cells aid in producing the pulmonary surfactant used in gas exchange. Further, the alveolar epithelium also comprises macrophages, which assist in disposing of fine particulate foreign matter such as dust, tar, and pathogens. Despite the diminutive size of the alveoli (being only approximately 250 μm), because an adult can have between 200 million and 400 million alveoli, the alveolar respiratory surface area can be from approximately 1,400 to about 1,600 square feet.

According to some embodiments disclosed herein, absorption of NSAIDs administered by DPI or MDI through the pulmonary capillaries and epithelium can provide an immediately effective treatment to address symptoms of thromboembolic events. One of the novel realizations of some embodiments is that the substantial first pass effect produced by oral administration of NSAIDs, such as aspirin, can be avoided through administration by dry powder inhaler. In addition, there has hitherto been no teaching or suggestion regarding the pharmacokinetics of dry powder delivery of a NSAID, such as aspirin, and the possible metabolism or inactivation of the drug as it encounters the endothelial tissue of the pulmonary capillaries.

The delivery of a NSAID by DPI or MDI is a complex and unpredictable technological area that has not provided straightforward or expected results to a person of skill in the art. Accordingly, there has been no reason for a person of skill to believe that a combination of prior systems or treatment methods could produce the embodiments disclosed herein. For example, some embodiments herein recognize an unexpected result that as a drug crosses the endothelium of pulmonary arteries and alveoli, the first pass effect is minimized and results in a much lower rate of the activation of the drug than in other drug delivery pathways.

The endothelium of the pulmonary capillaries serves as a barrier by selectively allowing materials to exit or enter the bloodstream. It would be expected that aspirin would be inactivated in the pulmonary capillaries, which are lined by endothelial cells. The endothelial cells are extremely metabolically active. Thus, a person of skill would expect that aspirin would be inactivated by the endothelium of the pulmonary capillaries. However, according to some embodiments disclosed herein, it is contemplated that as the powdered drug encounters the endothelium, the endothelium can metabolize or activate a much smaller portion of the powdered drug compared to the metabolism provided by the gut and liver. For example, after being transformed in the stomach to salicylic acid, as much as 80% of the salicylic acid is metabolized in the liver. Thus, only a small minority of the salicylic acid is bioavailable to the systemic blood stream.

However, it is contemplated that a vast majority of the salicylic acid metabolized from the inhaled aspirin powder will be bioavailable to the systemic blood stream. Thus, a dose of much less than that of a baby aspirin (e.g., less than 81 mg) can be provided by dry powder inhalation. This can provide a much lower dosage while providing a bioequivalent dosage.

Further, in accordance an aspect of some embodiments, it is contemplated that an analogous first pass effect may be experienced in the endothelium of the pulmonary capillaries. Accordingly, with regard to the provision of an inhaled dosage that is the bioequivalent of a baby aspirin administered orally, the inhaled dosage should account for some first pass effect experience through the endothelium of the pulmonary capillaries.

In accordance with some embodiments, the first pass effect through the endothelium of the pulmonary capillaries can be a minimum, which provides little overall effect on the inhaled dosage.

However, it is also contemplated that in some embodiments, the first pass effect through the endothelium of the pulmonary capillaries can be entirely negligible. Thus, the amount of the inhaled dosage need not be adjusted to compensate for first pass effect through the pulmonary capillaries.

Therefore, some embodiments recognize the unexpected result that even extremely low doses of aspirin (and likely other NSAIDs) can provide a significant therapeutic effect while providing de minimus or inconsequential side effects. For example, doses as low as 1 mg, 2 mg, 3 mg, 4 mg, or 5 mg of acetylsalicylic acid can be effective in reducing the risk of a thromboembolic event. Accordingly, the net benefits increased dramatically at significantly lower doses, according to some embodiments. These results and outcomes are unexpected given the complex and unpredictable nature of drug interactions in the body, drug delivery pathways, and microscopic drug structures. Finally, no teachings or other prior references disclose a system or process for achieving therapeutically beneficial results while substantially avoiding any negative side effects using DPI or MDI drug delivery mechanisms with microscopic NSAIDs.

In accordance with some embodiments, the dry powder administration of the NSAID, such as a salicylate like acetylsalicylic acid, can comprise particles having a median aerodynamic diameter of from about 1 μm to about 5 μm, as discussed above. The particles can be highly porous and demonstrate a sponge-like morphology or be a component of a carrier particle. The particles can also demonstrate a spheroidal shape, by which the shape and porous surface can serve to decrease the area of contact between particles, thereby leading to less particle agglomeration and more effective distribution throughout the lung. Dry powder technologies, such as PulmoSphere™, may be implemented in embodiments of the methods and systems disclosed herein.

Referring to FIG. 1, in a dry powder inhalation technique, a patient can use a dry powder inhaler 10 to inhale a powder formulation of a drug, such as a NSAID. The dose is effective to reduce a risk of a thromboembolic event in the patient. An aspect of some embodiments is the realization that because the lung is an efficient filter, it generally only permits particles having a size of less than 5 μm. For example, after the drug enters the main stem bronchus 20, the drug will enter each lung 22, 24. The drug can then pass through the bronchial trees 26, 28 until reaching the individual alveoli 30 in the lungs 22, 24, which are exceedingly numerous, as discussed below. Of each long Thus, the dry powder inhaler 10 can allow the patient to self administer a dosage of particles having a size of from about 1 μm and about 5 μm. In some embodiments, the particle size can be from about 2 μm to about 4 μm.

According to some embodiments, various types of inhalers can be used to provide the drug using a DPI or MDI delivery system. The dose administered can be effective to reduce a risk of a thromboembolic event in a patient.

For example, the dry powder inhaler 10 can comprise a mouthpiece, a reservoir for receiving the NSAID, and an actuation member for making available the NSAID for inhalation by a patient through the mouthpiece.

For example, FIGS. 2A-2F illustrate a DPI delivery device 100 having a mouthpiece 102 and a drug compartment 104. The drug compartment 104 can be inserted into an inhaler body cavity 110.

For example, as shown in FIG. 2B, the drug compartment 104 can be inserted into the body cavity 110 into a stowed position 120 for storage purposes. However, the drug compartment 104 can also be moved to a first position 122, shown in FIG. 2C, in which a first receptacle 140 of the drug compartment 104 is aligned with a mouthpiece airway 142. In this first position 122, the drug contained in the first receptacle 140 can be delivered through the mouthpiece airway 142 to be inhaled by the patient, as illustrated in FIG. 2D.

Additionally, as shown in FIG. 2E, the drug compartment 104 can be moved to a second position 124 in which a second receptacle 144 is aligned with the mouthpiece airway 142. Thus position, the drug contained in the second receptacle 144 can be inhaled by the patient, as illustrated in FIG. 2F.

In the process of breathing, the lungs are normally continuously exposed to materials present in the environment of a variety of sizes. This can include pollens (20-90 μm), bacteria (0.2-200 μm), and smoke particulates (0.01-1 μm). Deposition of a particular particle depends on a number of factors, including the size and density of the particle, as well as the velocity of flow of air into and out of the lungs, and the resident time of the particle in the respiratory system. Moreover, the human body has developed systems to protect against adverse effects of some of these inhaled substances, including such processes as phagocytosis. Thus, one factor to consider when designing systems and methods for delivering a pharmaceutical compound via inhalation is the effect that particle size has on the location in the respiratory tract where drug particles are likely to become deposited after inhalation.

Particles that enter the lungs are deposited along the course of the respiratory tract by impaction, sedimentation and diffusion. Often, the behavior of particles within an airflow stream can be described by aerodynamic diameter, as described in detail herein. Like the Reynold's number concept in aerodynamics, two particles having the same aerodynamic diameter will behave fundamentally the same in an airflow, regardless of their actual geometric (i.e., physical) size.

Previously it has been shown that particle size, or more accurately, aerodynamic diameter, significantly affects the location within the respiratory system where particles are most likely to become deposited after inspiration. For example, Heyder et al. (J. Aerosol. Sci. 17, 811-825, 1986) examined deposition of particles ranging in size from 5 nm to 15 μm in the respiratory tract. Their studies indicated that particles with an aerodynamic diameter greater than 5 μm deposit predominantly by inertial impaction in the mouth and upper airways. Smaller particles, (aerodynamic diameter ranging from 1-5 μm) deposit deeper in the lungs by impaction and sedimentation, while very small particles (aerodynamic diameter<1 μm), mainly remain suspended in the airflow and are exhaled.

Others have obtained similar results, suggesting that for delivery of drugs to the lungs, particles with an median aerodynamic diameter of about 2 μm are likely to be efficiently deposited in the alveolar spaces, with fractional deposition approaching 90% of the delivered particle dose (Byron, 1986, J. Pharm. Sci. 75(5), 433-438). In contrast, where particles have an median aerodynamic diameter ranging from 5-10 μm, only about 10% of the delivered dose will deposit in the alveoli, with about 40% depositing in the airways, and the remainder in the oral cavity and pharynx. Where median aerodynamic diameter is 15 μm or greater, particles deposit predominantly in the oral cavity and pharynx. Given the proximity of the alveolar epithelium to the systemic circulation, and the known benefit of delivering drugs to the lungs in order to avoid loss of a pharmaceutical agent through hydrolysis in the gut, or first pass effects due to processing in the liver, there is thus an advantage gained by designing a powdered drug composition that will be most effectively delivered to and deposited in the respiratory tract, and in particular the alveolar spaces.

Further advantages are gained by deposition of drugs in the alveolar spaces. For example, their large effective surface area spaces, and the reduced thickness of the alveolar epithelium, provides nearly immediate transfer of a drug to the circulatory system. Similarly, as the blood leaving the alveolar capillaries first travels back to the heart via the pulmonary vein, significant levels of a therapeutic molecule can be achieved in the vicinity of the heart nearly immediately. This is a particular advantage in designing treatments for cardiovascular conditions as in the present case.

Thus, an anti-thromboembolic agent such as an NSAID can be delivered at a higher plasma concentration than would otherwise be possible with an equivalent amount of an orally administered dose of the agent, and these levels can be achieved more rapidly by delivery to the lungs as compared to oral administration. Thus, those of skill in the art will appreciate that it will be possible to achieve circulating plasma levels of an NSAID in the coronary circulation effective to reduce the risk of a thromboembolic event, with a lower a administered dosage than would be required if the NSAID were taken orally as per the current recommendation of physicians.

As described herein, one aspect of the subject technology provides an apparatus and method for providing a therapeutically effective dose of an NSAID in order to reduce the risk of a thromboembolic event. As discussed above, the general approach is to deliver an NSAID in a pharmaceutically acceptable powdered form (e.g., Acetylsalicylic acid, and/or derivatives thereof "ASA") by means of an inhaler. However, there are a number of challenges in delivering therapeutically effective amounts of an NSAID by a dry powder inhalations system.

One challenge in designing such treatment system is the limit in terms of the size of the dose that can be comfortably tolerated by the patient. For example, in some cases, it has been shown that about 40 to about 50 mg of powdered compound can be comfortably delivered in a single inhaled dose. Coincidentally, no currently available inhaler apparatus is capable of delivering more than about 50 mg of a powder per delivery. However, the recommended dosage for ASA in order to treat suspected symptoms consistent with impending myocardial infarct are to chew two 81 mg tablets of ASA. Thus, the recommended dose for such treatment is about 160 mg. This suggests that in order to provide the identical amount of ASA as recommended by oral administration, a patient may have to take as many as four inhaled doses within the same time period. Studies have shown that patients can realistically take five inhaled doses within one minute, using currently available inhaler technology.

As discussed above, there is a general trend that deposition of particle in the alveolar spaces increases as particle size is reduced. Studies on nanoparticle distribution have shown that inhaled nanoparticles having a size <100 nm are desirable for alveolar deposition as well as for minimizing lung phagocytosis (Hoet et al., 2004, J. Nanbiotechnol. 2, doi:10.1186/1477-3155-2-12). Nanoparticles provide additional advantages in terms of dispersion of the active compound and ultimately in the rate of uptake as compared to coarser preparations, the most obvious of which is that smaller particles tend to disperse and solubilize faster than larger ones. However, particles of nanometer size are not optimal for use in the delivery of a powdered pharmaceutical, as they tend not to deposit efficiently, but remain suspended in the airflow and are expelled upon exhalation.

One way in which to overcome this problem is through the use of methods to produce particles comprising aggregates of nanoparticles having optimal average aerodynamic size for efficient alveolar deposition. For example, Hadinoto et al. (2004, Int. J. Pharma., doi: 10.1016/j.ijpharm.2007.03.035) have shown that large hollow shells comprising nanoparticles can be produced by a spray-drying method. While these particles have a large geometric diameter (10-15 μm), they have a small aerodynamic diameter (1-3 μm) that is desirable for delivery of compounds to deeper regions of the lungs. Moreover, these large hollow shells rapidly disaggregate into the constituent nanoparticles providing rapid release of the pharmaceutical agent. In addition, Hadinoto et al. have shown that this method is adaptable to producing preparations of ASA for used in powder inhaler devices. Thus, using these methods in combination with subject technology it is possible to achieve ASA particles of an aerodynamic size for deposition to alveolar spaces, and where over 90% of the drug is released from the particles within 30 minutes.

However, despite the ability to make particles of an optimal size, there is an additional problem in preparing pharmaceutical compositions for use via inhalation. Typically, it has been observed that powders of uniform size, tend to clump and form larger aggregates via a phenomenon known as bridging. Particle when bridged behave aerodynamically as much larger particles, and as discussed above, will tend not to reach the alveolar spaces, which are desired for optimum rapid delivery of the drug of interest. In order to reduce aggregation of the pharmaceutically active agent, drugs are often blended with excipient particles such as lactose for example in order to inhibit aggregation. While the addition of excipients is an effective method to inhibit aggregation, their addition reduces the amount of the pharmaceutically active compound per measured inhaled dose. The result would be that a patient would have to take a greater number of doses in order to achieve the same intake of the pharmaceutically active compound. In an emergency situation, this may be impractical. For example, if a preparation were made that was 50% ASA ingredient and 50% excipient, with a limit of 40 mg of powder per dose, a person would have to inhale about 8 doses in order to take the recommended 162 mg of ASA for treatment of symptom suggestive of an impending infarct. Such a situation may make dry powder inhalers less practical.

However, in the present case, the inventors have now discovered that mixing particles of the same active ingredient (e.g., ASA), using batches of particles having different size distributions, can reduce bridging. For example, while a composition having a relatively uniform particle size will aggregate, providing a blended composition having some particles with a median aerodynamic diameter in a range from about 1 μm to about 5 μm, other particles with a median aerodynamic diameter in a range from about 5 μm to about 15 μm, and still other particles with a median aerodynamic diameter greater than about 15 μm, will inhibit aggregation and maintain the deposition characteristics of the preparation. In effect, the pharmaceutically active compound is used to replace the function of an excipient (such as lactose) with respect to preventing aggregation during storage of the medicament. To the knowledge of the inventor, no one has considered using the pharmaceutically active ingredient as its own excipient for the purposes of inhibiting aggregation.

In addition, and unlike many other drugs, NSAIDs, and in particular ASA, are able to enter the circulatory system effectively through routes other than through the epithelium of the alveoli. Notably, ASA is able to enter the body by absorption through the mucosal layers of the oral cavity, as well as the pharynx and undoubtedly the epithelium of the airways. Thus, regardless of particle size, it will be appreciated that by providing an inhalable form of ASA, the inhaled dosage can be substantially taken up into the systemic circulation, and be effective to reduce the risk of a thromboembolic event.

In addition, by selecting the proportions of the various particle sizes, one can provide formulations that are faster or slower acting, based on the location of where the drug is ultimately deposited. For example, in some embodiments it may be desirable to provide a preparation that comprises 80% ASA particles with a median aerodynamic diameter of about 1 µm to about 5 µm, and about 20% of particles with a median aerodynamic diameter of at least 15 µm. Other combinations are possible as well, and those of skill in the art will readily appreciate that faster acting preparations will comprise proportionately more smaller particles, while slower acting preparations will comprise proportionately more large particles. Thus, using the apparatus and methods described herein it is therefore possible to provide a therapeutically effective dose of an NSAID such as ASA via the respiratory tract, at least as rapidly as can be achieved by oral dosing.

Where a slower acting dosages form was desired, the formulation could include increasing fractions of particles with a median aerodynamic diameter in the range from about 5 µm to about 10 µm, or 15 µm or greater. These preparations would result in deposition in either the airways or oral cavity and pharynx and thus provide a more gradual increase in circulating levels of ASA and its metabolic derivatives.

In either case, the subject technology provides formulations that can deliver ASA and its pharmacologically active metabolic byproducts (e.g., salicylate) to the systemic circulation at least as quickly if not more quickly than can be accomplished via oral administration. In addition, the present formulations are effective to deliver ASA and its pharmacologically active metabolic byproducts to the systemic circulation at levels at least equal to that observed after oral administration of an equivalent dose of ASA.

For example, pharmacokinetic studies show that after oral administration of ASA peak plasma levels are achieved after about 20 minutes, after which they rapidly decline due to the relatively short elimination half-life (15-20 minutes). By comparison, plasma levels of the primary pharmacologically active metabolite salicylate, increase for a period of about 45 minutes following administration of ASA, and remain elevated for much longer due to its significantly longer elimination half-life (2-3 hr) (Dressman et al., 2012, Biowaiver Monograph for Immediate-Release Solid Oral Dosage Forms: Acetylsalicylic Acid, doi 10.1002/jps.2312).

Significantly, the pharmacokinetic behavior of ASA has been found to be linear over a dosage range from 30-400 mg. Extrapolating from these data, one would therefore expect that peak circulating plasma levels of ASA and SA would be approximately 4 mcg/mL and 10 mcg/mL respectively and with the same temporal kinetics as discussed above.

Accordingly, one aspect of the subject technology provides a dry powder that comprises a mixture of particles of various sizes.

For example, the dry powder can comprise particles of large sizes, as measured by VMGD (e.g., VMGD≥15 µm, such as ≥20 µm or 20-30 µm) and of small sizes, measured by VMGD (e.g., VMGD≤5 µm, such as 1-3 µm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 10 µm or less, preferably about 5 µm or less. Particles of 10 µm or less generally can reach lungs, and particles of 5 µm or less (e.g., 1-3 µm) generally can reach alveoli.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of between about 5 µm to about 20 µm, preferably between about 5 µm to about 15 µm, or between about 5 µm to about 10 µm.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 15 µm or more, preferably 20 µm or more.

The above features can be combined. For example, the dry power can comprise about 50% of particles of about 5 µm or less (VMGD), about 25% of particles of about 5 to about 15 µm (VMGD), and about 25% of particles of about 15 µm or more (VMGD).

The dry powder can also comprise a mixture of particles having various mass median aerodynamic diameters (MMAD). For example, the dry powder can comprise particles of large sizes (e.g., MMAD≥15 µm, such as ≥20 µm or 20-30 µm) and of small sizes (e.g., MMAD≤5 µm, such as 1-3 µm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 10 µm or less, preferably about 5 µm or less. Particles of 10 µm or less generally can reach lungs, and particles of 5 µm or less (e.g., 1-3 µm) generally can reach alveoli.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of between about 5 μm to about 20 μm, preferably between about 5 μm to about 15 μm, or between about 5 μm to about 10 μm.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 15 μm or more, preferably 20 μm or more.

The above features can be combined. For example, the dry power can comprise about 50% of particles of about 5 μm or less (MMAD), about 25% of particles of about 5 to about 15 μm (MMAD), and about 25% of particles of about 15 μm or more (MMAD).

In some embodiments, the dry powder does not comprise, or does not substantially comprise, an excipient. In some embodiments, the dry powder does not comprise, or does not substantially comprise, an anti-aggregation (or anti-bridging) excipient.

In certain embodiments, the dry powder comprises a mixture of particles of various sizes, and is effective to substantially prevent or reduce particle bridging. In certain embodiment, at least about 40%, at least about 45%, at least about 50%, at least about 55%, at least about 60%, at least about 65%, at least about 70%, at least about 75%, at least 80%, at least about 85%, or at least about 90% of the NSAID (such as acetylsalicylic acid) in the dry powder is delivered to the alveolar spaces of a lung.

6. Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), and other suitable methods. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles can be spray dried. Suitable spray-drying techniques are described, for example, by K. Masters in "Spray Drying Handbook", John Wiley & Sons, New York (1984); and spray drying techniques developed by BUCHI Laboratory Equipment or GEA Niro drying technology. Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 100° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the subject technology, generally, a solution, emulsions or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophillic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

In one example, respirable dry particles that comprise acetylsalicylic acid and sodium citrate are prepared by spray drying.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions (such as phosphate buffer).

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable particles can also be produced by jet-milling. See, e.g., techniques developed by Apex Process Technology or Jetpharma SA. Jet milling is a process of using highly compressed air or other gasses, usually in a vortex motion, to impact fine particles against each other in a chamber. Jet mills are capable of reducing solids to particle sizes in the low-micron to submicron range. The grinding energy is created by gas streams from horizontal grinding air nozzles. Particles in the fluidized bed created by the gas streams are accelerated towards the centre of the mill, colliding with slower moving particles. The gas streams and the particles carried in them create a violent turbulence and as the particles collide with one another they are pulverized.

Wet polishing is a process that combines a technology to attain a small particle size (either a bottom up technique such as controlled crystallization or nanocrystallization or top down technique such as high shear mixing or high pressure homogenization) with a suitable isolation technology (for example spray drying or filtration with a drying process). See, e.g., techniques developed by Hovione. These combinations can be used to tune the particle size and morphology to meet specific drug delivery needs. The method allows control of particle size distribution with tight spans and in-process sampling, and maintains crystalline state (little or no amorphous content).

Wet polishing technique can be repeated multiple times to achieve a particular size of about 500 nanometers or less.

Particles described herein can be encapsulated, e.g., by a pharmaceutical excipient such as lactose, sugar, or a polymer.

The above techniques can be combined. For example, after going through the wet polishing process, the particles can go through a spray drying process (e.g., for the purpose of micro-encapsulation).

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 µm VMGD.

The diameter of the respirable dry particles, for example, their VMGD, can be measured using an electrical zone sensing instrument such as a Multisizer Ile, (Coulter Electronic, Luton, Beds, England), or a laser diffraction instrument such as a HELOS system (Sympatec, Princeton, N.J.). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor and the multi-stage liquid impinger (MSLI) methods. The methods and instruments for measuring particle aerodynamic diameter are well known in the art.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopia convention, Rockville, Md., $10^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cut-offs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages of the eight-stage ACI and allows for the collection of two separate powder fractions. Specifically, a two-stage collapsed ACI is calibrated so that the fraction of powder that is collected on stage one is composed of respirable dry particles that have an aerodynamic diameter of less than 5.6 µm and greater than 3.4 µm. The fraction of powder passing stage one and depositing on a collection filter is thus composed of respirable dry particles having an aerodynamic diameter of less than 3.4 μm. The airflow at such a calibration is approximately 60 L/min.

The FPF(<5.6) has been demonstrated to correlate to the fraction of the powder that is able to make it into the lung of the patient, while the FPF(<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF_TD(<5.0) is the ratio of the interpolated amount of powder depositing below 5.0 μm on the ACI to the nominal dose. The FPF_RD(<5.0) is the ratio of the interpolated amount of powder depositing below 5.0 μm on the ACI to either the gravimetric recovered dose or the analytical recovered dose.

Another way to approximate emitted dose is to determine how much powder leaves its container, e.g. capture or blister, upon actuation of a dry powder inhaler (DPI). This takes into account the percentage leaving the capsule, but does not take into account any powder depositing on the DPI. The emitted dose is the ratio of the weight of the capsule with the dose before inhaler actuation to the weight of the capsule after inhaler actuation. This measurement can also be called the capsule emmited powder mass (CEPM)

A Multi-Stage Liquid Impinger (MSLI) is another device that can be used to measure fine particle fraction. The Multi-stage liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The subject technology also relates to a respirable dry powder or respirable dry particles produced using any of the methods described herein.

The respirable dry particles of the subject technology can also be characterized by the chemical stability of the salts or the excipients that the respirable dry particles comprise. The chemical stability of the constituent salts can effect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the subject technology include salts that are generally stable over a long period time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. The maltodextrin may act as an amorphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore their dispersibility if agglomerates formed during the crystallization process, such as by passing the particles through a cyclone to break apart the agglomerates. Another possible approach is to optimize around process conditions that lead to manufacturing particles that are more crystalline and therefore more stable. Another approach is to use different excipients, or different levels of current excipients to attempt to manufacture more stable forms of the salts.

The respirable dry particles and dry powders described herein are suitable for inhalation therapies. The respirable dry particles may be fabricated with the appropriate material, surface roughness, diameter and tap density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}$/LPM, Q is the steady flow rate in L/min and V is the inhaled air volume in L.

Healthy adult populations are predicted to be able to achieve inhalation energies ranging from 2.9 to 22 Joules by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19, (4), p. 456-465, 2006) who found adults averaging 2.2 L inhaled volume through a variety of DPIs.

Dry powder particles can also be prepared using cone-jet mode of electrohydrodynamic atomization, as described by Li et al., Chemical Engineering Science 61 (2006) 3091-3097. For example, an aspirin solution flowing through a needle can be subjected to an electric field to generate droplets. The method is said to generating a near-monodispersed distribution of droplet relics, leading to form aspirin particulate crystals.

7. Methods of Treatment

In other aspects, the subject technology is a method for treating (including prophylactic treatment or reducing the risk) of a cardiovascular disease (such as thrombosis), comprising administering to the respiratory tract of a subject in need thereof an effective amount of respirable dry particles or dry powder, as described herein.

Cardiovascular diseases include, for example, atherosclerosis, coronary artery disease (CAD), angina pectoris (commonly known as "angina"), thrombosis, ischemic heart disease, coronary insufficiency, peripheral vascular disease, myocardial infarction, cerebrovascular disease (such as stroke), transient ischemic attack, arteriolosclerosis, small vessel disease, elevated cholesterol, intermittent claudication or hypertension.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCapss®, TwinCaps®, XCaps (Hovione, Loures, Portugal), Inhalators® (Boehringer-Ingelheim, Germany), Aerolizer® (Novartis, Switzerland), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 μl, 770 μl, 680 μl, 480 μl, 360 μl, 270 μl, and 200 μl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders, are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well-known that particles with an aerodynamic diameter of about 1 micron to about 3 μm, can be delivered to the deep lung. Larger aerodynamic diameters, for example, from about 3 μm to about 5 μm can be delivered to the central and upper airways.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 μm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 μm or less), the size distribution of the inhaled powder may have an MMAD of greater than 5 μm, leading to enhanced oral cavity deposition.

Therefore, it is desirable to have a powder in which the particles are small (e.g., MMAD of 5 μm or less, e.g. between 1 to 5 μm), and are highly dispersible (e.g. ¼ bar or alternatively, 0.5/4 bar of 2.0, and preferably less than 1.5). More preferably, the respirable dry powder is comprised of respirable dry particles with an MMAD between 1 to 4 μm or 1 to 3 μm, and have a ¼ bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt(envelope density)). If it is desired to deliver a high unit dose of salt using a fixed volume dosing container, then, particles of higher envelop density are desired. High envelope density allows for more mass of powder to be contained within the fixed volume dosing container. Preferable envelope densities are greater than 0.1 g/cc, greater than 0.25 g/cc, greater than 0.4 g/cc, greater than 0.5 g/cc, and greater than 0.6 g/cc.

The respirable dry powders and particles of the subject technology can be employed in compositions suitable for drug delivery via the respiratory system. For example, such compositions can include blends of the respirable dry particles of the subject technology and one or more other dry particles or powders, such as dry particles or powders that contain another active agent, or that consist of or consist essentially of one or more pharmaceutically acceptable excipients.

Respirable dry powders and dry particles suitable for use in the methods of the subject technology can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the subject technology, most of the mass of respirable dry powders or particles deposit in the deep lung. In another embodiment of the subject technology, delivery is primarily to the central airways. In another embodiment, delivery is to the upper airways.

The respirable dry particles or dry powders of the subject technology can be delivered by inhalation at various parts of the breathing cycle (e.g., laminar flow at mid-breath). An advantage of the high dispersibility of the dry powders and dry particles of the subject technology is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they they are released later in the inhalation.

The dry powders of this subject technology provide advantages for targeting the timing of drug delivery in the breathing cycle and also location in the human lung. Because the respirable dry powders of the subject technology can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

Suitable intervals between doses that provide the desired therapeutic effect can be determined based on the severity of the condition, overall well being of the subject and the subject's tolerance to respirable dry particles and dry powders and other considerations. Based on these and other considerations, a clinician can determine appropriate intervals between doses. Generally, respirable dry particles and dry powders are administered once, twice or three times a day, as needed.

In some embodiments the amount of NSAID delivered to the respiratory tract (e.g., lungs, respiratory airway) is about 0.001 mg/kg body weight/dose to about 2 mg/kg body weight/dose, about 0.002 mg/kg body weight/dose to about 2 mg/kg body weight/dose, about 0.005 mg/kg body weight/dose to about 2 mg/kg body weight/dose, about 0.01 mg/kg body weight/dose to about 2 mg/kg body weight/dose, about 0.02 mg/kg body weight/dose to about 2 mg/kg body weight/dose, about 0.05 mg/kg body weight/dose to about 2 mg/kg body weight/dose, about 0.075 mg/kg body weight/dose to about 2 mg/kg body weight/dose, about 0.1 mg/kg body weight/dose to about 2 mg/kg body weight/dose, about 0.2 mg/kg body weight/dose to about 2 mg/kg body weight/dose, about 0.5 mg/kg body weight/dose to about 2 mg/kg body weight/dose, or about 0.75 mg/kg body weight/dose to about 2 mg/kg body weight/dose.

In certain embodiments, at least about 50%, at least about 60%, at least about 70%, at least about 75%, at least about 80%, at least about 85%, at least about 90%, at least about 95%, or at least about 99%, of the administered acetylsalicylic acid reaches the systemic circulation of a subject within about 60 minutes upon administration, or within about 40 minutes upon administration, or within about 30 minutes upon administration, or within about 20 minutes upon administration, or within about 15 minutes upon administration.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 30 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 40 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 50 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 80 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 162 mg of acetylsalicylic acid.

The doses of acetylsalicylic acid administered in order to achieve a level (or an average level among a population of patients) that is substantially the same, or higher as compared to those delivered by oral administration of about 30 mg, about 40 mg, about 50 mg, about 80 mg, or about 182 mg of acetylsalicylic acid can be determined by conventional methods. The dosing, administration techniques and schedules are known in the art are within the ability of the skilled clinician. For example, the serum level of acetylsalicylic acid, or a metabolite thereof, in a subject (or average serum level among a population of subjects) can be determined by convention pharmacokinetic or pharmacodynamics studies.

In certain embodiments, the method and delivery devices described herein can deliver acetylsalicylic acid to the systemic circulation such that circulating plasma level of acetylsalicylic acid is at least about 1 mcg/mL, at least about 2 mcg/mL, at least about 3 mcg/mL, at least about 4 mcg/mL, at least about 5 mcg/mL, or at least about 6 mcg/mL within about 60 minutes upon administration, or within about 40 minutes upon administration, or within about 30 minutes upon administration, or within about 20 minutes upon administration, or within about 15 minutes upon administration.

In certain embodiments, the method and delivery devices described herein can deliver acetylsalicylic acid to the systemic circulation such that circulating plasma level of salicylate is about 8 mcg/mL, about 9 mcg/mL, about 10 mcg/mL, about 11 mcg/mL, about 12 mcg/mL, about 15 mcg/mL, within about 60 minutes upon administration, or within about 40 minutes upon administration, or within about 30 minutes upon administration, or within about 20 minutes upon administration, or within about 15 minutes upon administration.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It is to be understood that, while the subject technology has been described in conjunction with the detailed description, thereof, the foregoing description is intended to illustrate and not limit the scope of the subject technology. Other aspects, advantages, and modifications of the subject technology are within the scope of the claims set forth below. The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

What is claimed is:

1. A method of treating thrombosis or reducing risk of a thromboembolic event in a subject in need thereof, the method comprising administering by pulmonary delivery to the subject dry particles free of excipients from within a dry powder inhaler, wherein the dry particles in the inhaler before the administering are provided in a capsule or blister and consist of acetylsalicylic acid or a pharmaceutically acceptable salt thereof, wherein the dry particles have a mass median aerodynamic diameter (MMAD) of less than 5 µm, and wherein the dry particles deliver at least 50% of administered acetylsalicylic acid to systemic circulation of the subject with about 15 minutes after the administering.

2. The method of claim 1, wherein the dry powder formulation delivers at least 60% of administered acetylsalicylic acid to systemic circulation of the subject within about 15 minutes of administration.

3. The method of claim 1, wherein the dry powder formulation delivers at least 70% of administered acetylsalicylic acid to systemic circulation of the subject within about 15 minutes of administration.

4. The method of claim 1, wherein the dry powder formulation delivers at least 80% of administered acetylsalicylic acid to systemic circulation of the subject within about 15 minutes of administration.

5. The method of claim 1, wherein the dose of acetylsalicylic acid administered to the subject is about 40 mg or less.

6. The method of claim 5, wherein the dose of acetylsalicylic acid administered to the subject is about 30 mg or less.

7. A method of treating thrombosis or reducing risk of a thromboembolic event in a subject in need thereof, the method comprising administering by pulmonary delivery to the subject dry particles free of excipients from within a dry powder inhaler, wherein the dry particles in the inhaler before the administering are provided in a capsule or blister and consist of acetylsalicylic acid or a pharmaceutically acceptable salt thereof, wherein the dry particles have a geometric diameter (VMGD) of less than 5 µm, and wherein the dry particles deliver at least 50% of administered acetylsalicylic acid to systemic circulation of the subject with about 15 minutes after the administering.

8. The method of claim 7, wherein the dry powder formulation delivers at least 60% of administered acetylsalicylic acid to systemic circulation of the subject within about 15 minutes of administration.

9. The method of claim 7, wherein the dry powder formulation delivers at least 70% of administered acetylsalicylic acid to systemic circulation of the subject within about 15 minutes of administration.

10. The method of claim 7, wherein the dry powder formulation delivers at least 80% of administered acetylsalicylic acid to systemic circulation of the subject within about 15 minutes of administration.

11. The method of claim 7, wherein the dose of acetylsalicylic acid administered to the subject is about 40 mg or less.

12. The method of claim 11, wherein the dose of acetylsalicylic acid administered to the subject is about 30 mg or less.

* * * * *